(12) United States Patent
Baxter et al.

(10) Patent No.: US 11,718,018 B2
(45) Date of Patent: Aug. 8, 2023

(54) 3D PRINTED MEDICAL DEVICES INCLUDING INTERNAL SHAPING

(71) Applicant: Medtronic, Inc., Minneapolis, MN (US)

(72) Inventors: Jonathan E. Baxter, Fridley, MN (US); Kristin M. Johnson, Circle Pines, MN (US); Gregory N. Nesseth, Forest Lake, MN (US); Jay T. Rassat, Otsego, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/390,260

(22) Filed: Jul. 30, 2021

(65) Prior Publication Data

US 2022/0032537 A1 Feb. 3, 2022

Related U.S. Application Data

(60) Provisional application No. 63/059,870, filed on Jul. 31, 2020.

(51) Int. Cl.
*B29C 64/118* (2017.01)
*B33Y 10/00* (2015.01)
(Continued)

(52) U.S. Cl.
CPC ....... *B29C 64/118* (2017.08); *A61M 25/0009* (2013.01); *A61M 25/0045* (2013.01); *B29C 64/209* (2017.08); *B29C 64/227* (2017.08); *B29C 64/321* (2017.08); *B33Y 10/00* (2014.12); *B33Y 30/00* (2014.12); *B33Y 40/00* (2014.12);
(Continued)

(58) Field of Classification Search
CPC ... B29C 64/118; B29C 64/209; B29C 64/227; B29C 64/321; B29C 64/393; B29C 64/241; A61M 25/0009; A61M 25/004
See application file for complete search history.

(56) References Cited

U.S. PATENT DOCUMENTS 2,764,148 A 9/1956 Sheldon
3,485,234 A 12/1969 Stevens
(Continued)

FOREIGN PATENT DOCUMENTS

CA 2998126 10/2018
EP 1053039 11/2000
(Continued)

OTHER PUBLICATIONS

International Preliminary Report on Patentability for PCT Application No. PCT/US2021/024640 dated Oct. 13, 2022, 10 pages.
(Continued)

*Primary Examiner* — Joseph S Del Sole
*Assistant Examiner* — Mohamed K Ahmed Ali
(74) *Attorney, Agent, or Firm* — Mueting Raasch Group

(57) ABSTRACT

Systems and methods for manufacturing elongate medical devices including internal components embedded between multiple jacket layers. The system including a heating cartridge, a heating element, a filament handling system, a substrate handling system, and a controller to feed and melt each of the filaments for forming the multiple jacket layers. The system may include a single heating cartridge adapted to make multiple passes to form a first and second jacket or multiple heating cartridges that sequentially form a first and second jacket.

17 Claims, 14 Drawing Sheets

(51) Int. Cl.
- *B33Y 30/00* (2015.01)
- *B33Y 40/00* (2020.01)
- *B33Y 80/00* (2015.01)
- *B29C 64/321* (2017.01)
- *B29C 64/209* (2017.01)
- *B29C 64/227* (2017.01)
- *B29C 64/393* (2017.01)
- *B33Y 50/02* (2015.01)
- *A61M 25/00* (2006.01)
- *B29L 31/00* (2006.01)

(52) U.S. Cl.
CPC ............ *B33Y 80/00* (2014.12); *B29C 64/393* (2017.08); *B29L 2031/7542* (2013.01); *B33Y 50/02* (2014.12)

(56) References Cited

U.S. PATENT DOCUMENTS

| | | | |
|---|---|---|---|
| 5,871,475 | A | 2/1999 | Frassica |
| 6,591,472 | B1 | 7/2003 | Noone et al. |
| 7,306,617 | B2 | 12/2007 | Majercak |
| 7,833,218 | B2 | 11/2010 | Lunn et al. |
| 7,909,033 | B2 | 3/2011 | Faram |
| 8,118,827 | B2 | 2/2012 | Duerig et al. |
| 8,509,916 | B2 | 8/2013 | Byrd et al. |
| 9,002,496 | B2 | 4/2015 | Elsey |
| 9,043,191 | B2 | 5/2015 | Grady et al. |
| 9,974,887 | B2 | 5/2018 | Eversull et al. |
| 10,254,499 | B1 | 4/2019 | Cohen et al. |
| 10,327,862 | B2 | 6/2019 | Lubinski |
| 10,442,175 | B2 | 10/2019 | Schlachter |
| 10,548,355 | B2 | 2/2020 | Volpis et al. |
| 10,610,666 | B2 | 4/2020 | Stern |
| 10,751,507 | B2 | 8/2020 | Palmer et al. |
| 2004/0002677 | A1 | 1/2004 | Gentsler |
| 2007/0005041 | A1 | 1/2007 | Frassica et al. |
| 2007/0060863 | A1 | 3/2007 | Goeken et al. |
| 2008/0262472 | A1 | 10/2008 | Lunn et al. |
| 2012/0149985 | A1 | 6/2012 | Frassica et al. |
| 2014/0284838 | A1 | 9/2014 | Pfeffer et al. |
| 2014/0361460 | A1 | 12/2014 | Mark |
| 2015/0217517 | A1 | 8/2015 | Karpas et al. |
| 2016/0096323 | A1 | 4/2016 | Fry et al. |
| 2016/0101262 | A1 | 4/2016 | Root et al. |
| 2016/0184233 | A1 | 6/2016 | Palomar-Moreno et al. |
| 2016/0207220 | A1 | 7/2016 | Hack et al. |
| 2016/0303347 | A1 | 10/2016 | Porter |
| 2017/0182290 | A1 | 6/2017 | Stern |
| 2017/0189553 | A1 | 7/2017 | Hunter |
| 2017/0259506 | A1 | 9/2017 | Ho et al. |
| 2018/0036123 | A1 | 2/2018 | Costello |
| 2018/0065320 | A1 | 3/2018 | Tyler |
| 2018/0117855 | A1 | 5/2018 | Girou et al. |
| 2018/0141274 | A1 | 5/2018 | Fink et al. |
| 2018/0168687 | A1 | 6/2018 | Drake et al. |
| 2018/0254099 | A1 | 9/2018 | Beydoun et al. |
| 2018/0289925 | A1 | 10/2018 | Palmer et al. |
| 2018/0370117 | A1 | 12/2018 | Gardiner et al. |
| 2019/0002625 | A1 | 1/2019 | Jiang et al. |
| 2019/0209080 | A1 | 7/2019 | Gullotti et al. |
| 2019/0240456 | A1 | 8/2019 | Pokorny et al. |
| 2019/0351185 | A1 | 11/2019 | Assouline et al. |
| 2019/0375149 | A1 | 12/2019 | Limem et al. |
| 2020/0080237 | A1 | 3/2020 | Vogt et al. |
| 2020/0093505 | A1 | 3/2020 | Sinelnikov et al. |
| 2021/0122115 | A1 | 4/2021 | Ramos |
| 2021/0236767 | A1 | 8/2021 | Warnock, Jr. et al. |
| 2021/0298730 | A1 | 9/2021 | Baxter et al. |
| 2022/0226636 | A1 | 1/2022 | Rassat et al. |
| 2022/0032002 | A1 | 2/2022 | Baxter et al. |
| 2022/0032003 | A1 | 2/2022 | Baxter et al. |

FOREIGN PATENT DOCUMENTS

| | | |
|---|---|---|
| KR | 101863192 | 6/2018 |
| WO | 2014/172545 | 10/2014 |
| WO | 2016/168505 | 10/2016 |
| WO | 2019/070899 | 4/2019 |

OTHER PUBLICATIONS

Ascend Medical Technologies, "Design Guidelines for 3D X-Fusion Technology", ascendmedtech.com/design-guidelines, retrieved Oct. 25, 2019, 3 pages.

Ascend Medical Technologies, "Engineering Capabilities", ascendmedtech.com/design-guidelines, retrieved Oct. 25, 2019, 7 pages.

Baxter et al., U.S. Appl. No. 17/215,842, filed Mar. 29, 2021.

Dilberoglu et al., "Current trends and research opportunities in hybrid additive manufacturing", The International Journal of Advanced Manufacturing Technology, 113, 2021, pp. 623-648.

Gardeski et al., U.S. Appl. No. 17/215,842, filed Mar. 29, 2021.

Gardeski et al., U.S. Appl. No. 63/001,832, filed Mar. 30, 2020.

Ramos et al., U.S. Appl. No. 17/081,815, filed Oct. 27, 2020.

Ramos et al., U.S. Appl. No. 62/927,092, filed Oct. 28, 2019.

Warnock Jr. et al., U.S. Appl. No. 17/162,101, filed Jan. 29, 2021.

Warnock Jr. et al., U.S. Appl. No. 62/970,561, filed Feb. 5, 2020.

International Search Report and Written Opinion from PCT/US2021/043795 dated Oct. 20, 2021, 14 pages.

International Search Report and Written Opinion from PCT Application No. PCT/US2021/024640 dated Sep. 13, 2021, 17 pages.

International Search Report and Written Opinion prepared for International Application No. PCT/US2021/043794, dated Nov. 23, 2021. 11 pages.

International Search Report and Written Opinion in PCT Application No. PCT/US2022/012966, dated Jun. 13, 2022, 19 pages.

International Search Report and Written Opinion in PCT Application No. PCT/US2021/043914, dated Dec. 20, 2021, 18 pages.

International Preliminary Report on Patentability for PCT/US2021/043914 dated Feb. 9, 2023 (14 pages).

3D PRINTED MEDICAL DEVICES INCLUDING INTERNAL SHAPING

This application claims the benefit of U.S. Provisional Patent Application Ser. No. 63/059,870 filed on Jul. 31, 2020, which is incorporated by reference herein in its entirety.

The disclosure generally relates to medical devices and, in particular, additive manufacturing or 3D printing of medical devices, such as catheters and implantable stimulation leads.

Medical catheters and leads are commonly used to access vascular and other locations within a body and to perform various functions at those locations, for example, delivery catheters may be used to deliver medical devices, such as implantable medical leads. A number of such medical devices are designed to be navigated through tortuous paths in a human body, such as through a patient's vasculature. Medical catheters and leads may be designed to be sufficiently flexible to move through turns, or curves, in the vasculature yet sufficiently stiff, or resilient, to be pushed through the vasculature. In many cases, such as those involving cardiovascular vessels, the route to the treatment or deployment site may be tortuous and may present conflicting design considerations that may require compromises between dimensions, flexibilities, material selection, operational controls and the like. These contrasting properties can present challenges in designing and manufacturing catheters. Existing manufacturing processes, such as conventional extrusion, may also limit options in designing and manufacturing catheters.

SUMMARY

The techniques of the present disclosure generally relate to additive manufacturing of medical devices, such as catheters and leads, that allows for further customization of the medical devices by providing an easier way to include components internal to the medical device. For example, the systems and techniques described herein may provide designing and printing an initial layer with internal spaces for components and then printing a finishing layer of the initial layer and components. These systems and techniques may allow for manufacturing more complex medical devices without increasing the complexity of manufacturing. Specifically, in one embodiment, the catheter may include internal grooves within which multiple lumen pull wires may be disposed. In another embodiment, the catheter may define an empty space for fluid travel during balloon inflation and may, e.g., include a bumped surface to help support the outer jacket.

Additionally, the medical devices (e.g., such as catheters) may be further customized through additive manufacturing to define lumens having a non-circular cross-sections (e.g., non-cylindrical shapes). For example, by utilizing systems and techniques described herein, a catheter jacket may be printed onto a combination of elongate substrates to define a lumen shape that corresponds to the combined elongate substrates. Specifically, two or more elongate substrates may be combined and arranged in a desired shape upon which the catheter jacket is printed to define the lumen having the desired shape. In some embodiments, a plurality of spacers may be used to separate the elongate substrates as desired. Further, the plurality of spacers may assist in the removal of the elongate substrates after the catheter jacket is formed by additive manufacturing.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
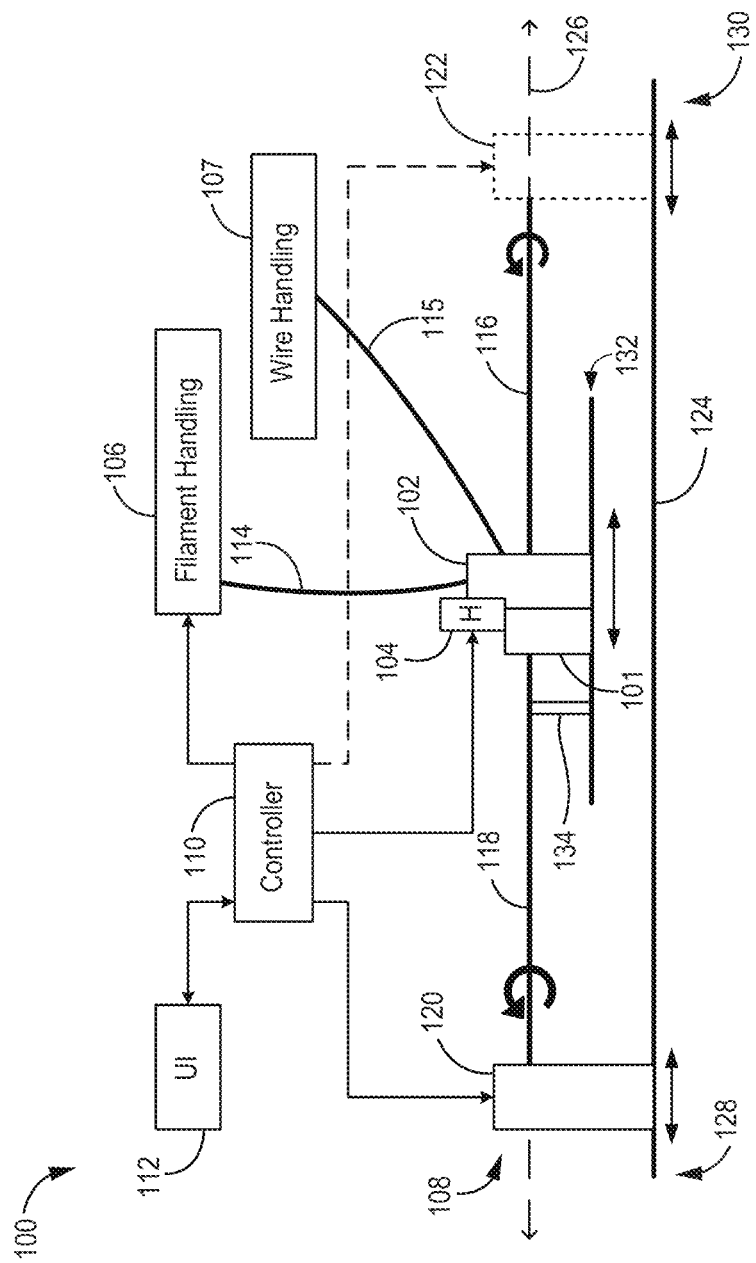
FIG. 1 is a conceptual diagram of an illustrative additive manufacturing system according to the present disclosure.

The present disclosure generally provides additive manufacturing systems and methods for medical devices, such as catheters and leads, that allows for providing more than one jacket or layer laid down to form the medical device. For example, one or more layers (e.g., an initial jacket or layer) may define shapes or structures within which internal components may be positioned and subsequent layers or jackets may cover or embed the internal components. The internal shapes and components included may be dictated by desirable functional characteristics or properties of the medical device. Specifically, components or empty space may be included on top of an initial print of filament material (e.g., a first layer or jacket) and a subsequent layer or jacket of filament material may be printed thereon. The printing may be done in multiple stages or as a part of a co-print with multiple printing head and tools, as described herein.

As used herein, the term "or" refers to an inclusive definition, for example, to mean "and/or" unless its context of usage clearly dictates otherwise. The term "and/or" refers to one or all of the listed elements or a combination of at least two of the listed elements.

As used herein, the phrases "at least one of" and "one or more of" followed by a list of elements refers to one or more of any of the elements listed or any combination of one or more of the elements listed.

As used herein, the terms "coupled" or "connected" refer to at least two elements being attached to each other either directly or indirectly. An indirect coupling may include one or more other elements between the at least two elements being attached. Either term may be modified by "operatively" and "operably," which may be used interchangeably, to describe that the coupling or connection is configured to allow the components to interact to carry out described or otherwise known functionality. For example, a controller may be operably coupled to a resistive heating element to allow the controller to provide an electrical current to the heating element.

As used herein, any term related to position or orientation, such as "proximal," "distal," "end," "outer," "inner," and the like, refers to a relative position and does not limit the absolute orientation of an embodiment unless its context of usage clearly dictates otherwise.

All scientific and technical terms used herein have meanings commonly used in the art unless otherwise specified. The definitions provided herein are to facilitate understanding of certain terms used frequently herein and are not meant to limit the scope of the present disclosure.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows one example of an additive manufacturing system 100 according to the present disclosure. The system 100 may be configured and used to produce a catheter, catheter component, lead, or subassembly. The system 100 may use or include consumable filament materials or pellet form resins having a wide variety of hardness levels. The system 100 may be configured to operate a wide variety of process conditions to produce catheters, catheter components, leads, or subassemblies using filaments or pellet form resins of various hardness levels. In general, the system 100 defines a distal region 128, or distal end, and a proximal region 130, or proximal end. The system 100 may include a platform 124 including a rigid frame to support one or more components of the system.

Further components of the system 100 may be shown as described in U.S. Pat. App. No. 62/927,092, entitled "ADDITIVE MANUFACTURING FOR MEDICAL DEVICES," which is herein incorporated by reference. For example, as shown in the illustrated embodiment, the system 100 may include one or more components, such as a heating cartridge 102, a heating element 104, a filament handling system 106, an optional wire handling system 107, a substrate handling system 108, a controller 110, and a user interface 112. The filament handling system 106 may be operably coupled to the heating cartridge 102. The filament handling system 106 may provide one or more filaments 114 to the heating cartridge 102. The optional wire handling system 107 may be used to provide one or more wires 115 to the heating cartridge 102. The heating element 104 may be operably coupled, or thermally coupled, to the heating cartridge 102. The heating element 104 may provide heat to melt filament material in the heating cartridge 102 from the one or more filaments 114 provided by the filament handling system 106. The optional wires 115 may not be melted by the heating cartridge 102. The substrate handling system 108 may be operably coupled to the heating cartridge 102. The substrate handling system 108 may provide a substrate 116 that extends through the heating cartridge. Melted filament material located in the heating cartridge 102 may be applied to the substrate 116. The substrate 116 or the heating cartridge 102 may be translated or rotated relative to one another by the substrate handling system 108. The substrate handling system 108 may be used to move the substrate 116 or the heating cartridge 102 relative to one another to cover the substrate 116 with the melted filament material to form a jacket 118. The optional wires 115 may be incorporated into the jacket 118 (e.g., molded into, bedded within, etc.). In one or more embodiments, the wire handling system 107 may be replaced with an intermediate component system positioned proximate the heating cartridge 102 and comprising one or more internal components (as will be described further herein) to be incorporated into the jacket 118. The intermediate component system may include a 3D printer, a robotic arm, a spool, etc. that positions or places the internal components at the desired location on the jacket 118 (e.g., between layers, within channels, etc.).

The substrate 116 may also be described as a mandrel or rod. The jacket 118 may be formed or deposited around the substrate 116. In some embodiments, the jacket 118 may be formed concentrically around the substrate 116. In one example, the jacket 118 is formed concentrically and centered around the substrate 116.

Figure 6:
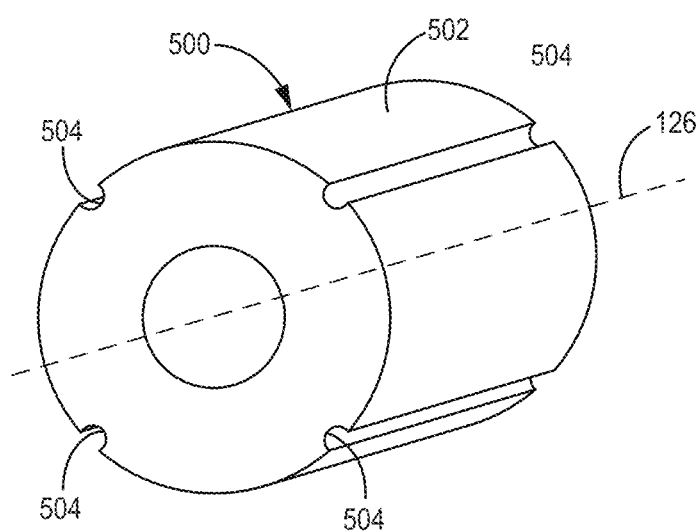
FIG. 6 is a conceptual diagram of an illustrative catheter jacket having a first jacket and cutouts that may be manufactured using the additive manufacturing system of FIG. 1.

When the system 100 is used to make a catheter or catheter component, the jacket 118 may be described as a catheter jacket. Some or all of the substrate 116 may be removed or separated from the jacket 118 and the remaining structure coupled to the jacket may form the catheter or catheter component, such as a sheath. One example of a catheter that may be formed by the system 100 is shown in FIG. 6.

The substrate 116 may be formed of any suitable material capable of allowing melted filament material to be formed thereon. In some embodiments, the substrate 116 is formed of a material that melts at a higher temperature than any of the filaments 114. One example of a material that may be used to form the substrate 116 includes stainless steel.

The controller 110 may be operably coupled to one or more of the heating element 104, the filament handling system 106, the substrate handling system 108, and the user interface 112. The controller 110 may activate, or initiate or otherwise "turn on," the heating element 104 to provide heat to the heating cartridge 102 to melt the filament material located therein. Further, the controller 110 may control or command one or more motors or actuators of various portions of the system 100. Furthermore, the controller 110 may control one or more motors or actuators the filament handling system 106 to provide one or more filaments 114. Further, the controller 110 may control one or more motors or actuators of the substrate handling system 108 to move one or both of the heating cartridge 102 or the substrate 116 relative to one another. Further still, the controller 110 may send or receive data to the user interface 112, for example, to display information or to receive user commands. Control of the components operably coupled to the controller 110 may be determined based on user commands received by the user interface 112. In some embodiments, the user commands may be provided in the form of a machine-readable code or coding language.

Any suitable implementation may be used to provide the substrate handling system 108. In some embodiments, the substrate handling system 108 may include one or more of a head stock 120, an optional tail stock 122, and one or more motors coupled to or included in the head stock or tail stock. One or both of the head stock 120 and the tail stock 122 may be coupled to the platform 124. A stock may be defined as a structure that holds or secures the substrate 116 during formation of the jacket 118. The head stock 120 is defined as the stock closest to the end of the substrate 116 where formation of the jacket 118 begins in the formation process. In the illustrated embodiment, the jacket 118 is shown proximal to the head stock 120 and distal to the heating cartridge 102.

When the substrate 116 is secured by one or both stocks 120, 122, the substrate is generally positioned to pass through a substrate channel defined by the heating cartridge 102. One or both stocks 120, 122 may include a clamp or other securing mechanism to selectively hold the substrate 116. Such a clamp may be operably coupled to a substrate motor. In some embodiments, the substrate motor may be used to control opening and closing of the clamp. In some embodiments, the substrate motor may be used to rotate the substrate 116 in a clockwise or counterclockwise direction about a longitudinal axis 126. A translation motor may be operably coupled between a stock 120, 122 and the platform 124. In some embodiments, the translation motor may be used to translate the stock 120, 122 in a longitudinal direction along the longitudinal axis 126. In some embodiments, the translation motor also may be used to translate the stock 120, 122 in a lateral direction different than the longitudinal axis 126. The lateral direction may be oriented substantially orthogonal, or perpendicular, to the longitudinal axis 126.

In some embodiments, the substrate handling system 108 may be configured to move the head stock 120 at least in a longitudinal direction (for example, parallel to the longitudinal axis 126) relative to the platform 124. The substrate 116 may be fed through the substrate channel of the heating cartridge 102 by movement of the head stock 120 relative to the platform 124. A distal portion of the substrate 116 may be clamped into the head stock 120. The head stock 120 may be positioned close to the heating cartridge 102 at the beginning of the jacket formation process. The head stock 120 may move distally away from the heating cartridge 102, for example in a direction parallel to the longitudinal axis 126. In other words, the head stock 120 may move toward the distal region 128 of the system 100 while pulling the secured substrate 116 through the heating cartridge 102. As the substrate 116 passes through the heating cartridge 102, melted filament material from the filament 114 may be formed or deposited onto the substrate 116 to form the jacket 118. The heating cartridge 102 may be stationary relative to the platform 124. In some embodiments, the tail stock 122 may be omitted.

In some embodiments, the substrate handling system 108 may be configured to move the heating cartridge 102 at least in a longitudinal direction (along the longitudinal axis 126) relative to the platform 124. The substrate 116 may be fed through the substrate channel of the heating cartridge 102. A distal portion of the substrate 116 may be clamped into the head stock 120. A proximal portion of the substrate 116 may be clamped into the tail stock 122. In one example, the heating cartridge 102 may be positioned relatively close to the head stock 120 at the beginning of the jacket formation process. The heating cartridge 102 may move proximally away from the head stock 120. The heating cartridge 102 may move toward the proximal region 130 of the system 100. As the heating cartridge 102 passes over the substrate 116, melted filament material may be deposited onto the substrate 116 to form a jacket. The head stock 120 and the tail stock 122 may be stationary relative to the platform 124. In another example, the heating cartridge 102 may start near the tail stock 122 and move toward the distal region 128.

One or more motors of the substrate handling system 108 may be used to rotate one or both of the substrate 116 and the heating cartridge 102 relative to one another. In some embodiments, only the substrate 116 may be rotated about the longitudinal axis 126. In some embodiments, only the heating cartridge 102 may be rotated about the longitudinal axis 126. In some embodiments, both the substrate 116 and the heating cartridge 102 may be rotated about the longitudinal axis 126.

The heating cartridge 102 may be part of a subassembly 132. The subassembly 132 may be coupled to the platform 124. In some embodiments, one or more motors of the substrate handling system 108 may be coupled between subassembly 132 and the platform 124 to translate or rotate the subassembly 132, including the heating cartridge 102, relative to the platform 124 or the substrate 116. In some embodiments, one or more motors of the substrate handling system 108 may be coupled between a frame of the subassembly 132 and the heating cartridge 102 to translate or rotate the heating cartridge relative to the platform 124.

In some embodiments, the substrate 116 may be rotated about the longitudinal axis 126 relative to the heating cartridge 102 to facilitate forming certain structures of the jacket. In one example, the substrate 116 may be rotated by one or both of the head stock 120 and the tail stock 122 of the substrate handling system 108. In another example, the heating cartridge 102 or subassembly 132 may be rotated by the substrate handling system 108.

The system 100 may include one or more concentricity guides 134. The concentricity guide 134 may facilitate adjustments to the concentricity of the jacket around the substrate 116 before or after the substrate passes through the heating cartridge 102. The concentricity guide 134 may be longitudinally spaced from the heating cartridge 102. In some embodiments, the spacing may be greater than or equal to 1, 2, 3, 4, or 5 cm. The spacing may be sufficient to allow the jacket 118 to cool down and no longer be deformable. In some embodiments, one or more concentricity guides 134 may be positioned distal to the heating cartridge 102 and to engage the jacket 118. In some embodiments, one or more concentricity guides 134 may be positioned proximal to the heating cartridge 102 to engage the substrate 116. The concentricity guide 134 may mitigate drooping of the substrate 116 and may mitigate susceptibility to eccentricity in the alignment of the stock 120, 122 and the heating cartridge 102.

Any suitable implementation may be used to provide the filament handling system 106. One or more filaments 114 may be loaded into the filament handling system 106. For example, filaments 114 may be provided in the form of wound coils. Filaments 114 may be fed to the heating cartridge 102 by the filament handling system 106. In some embodiments, the filament handling system 106 may include one, two, or more pinch rollers to engage the one or more filaments 114. In some embodiments, the filament handling system 106 may include one or more motors. The one or more motors may be coupled to the one or more pinch rollers to control rotation of the pinch rollers. The force exerted by the motors onto the pinch rollers and thus onto the one or more filaments 114 may be controlled by the controller 110.

In some embodiments, the filament handling system 106 may be configured to feed the filaments 114 including at least a first filament and a second filament. The jacket 118 may be formed from the material of one or both of the filaments 114. The filament handling system 106 may be capable of selectively feeding the first filament and the second filament. For example, one motor may feed the first filament and another motor may feed the second filament. Each of the motors may be independently controlled by the controller 110. Selective, or independent, control of the feeds may allow for the same or different feed forces to be applied to each of the filaments 114.

The filaments 114 may be made of any suitable material, such as polyethylene, PEBAX elastomer (commercially available from Arkema S.A. of Colombes, France), nylon 12, polyurethane, polyester, liquid silicone rubber (LSR), or PTFE.

The filaments 114 may have any suitable Shore durometer. In some embodiments, the filaments 114 may have, or define, a Shore durometer suitable for use in a catheter. In some embodiments, the filaments 114 have a Shore durometer of at least 25 A and up to 90 A. In some embodiments, the filaments 114 have a Shore durometer of at least 25 D and up to 80 D.

In some embodiments, the filament handling system 106 may provide a soft filament as one of the filaments 114. In some embodiments, a soft filament may have a Shore durometer less than or equal to 90 A, 80 A, 70 A, 80 D, 72 D, 70 D, 60 D, 50 D, 40 D, or 35 D.

In some embodiments, the filament handling system 106 may provide a hard filament and a soft filament having a Shore durometer less than the soft filament. In some embodiments, the soft filament has a Shore durometer that is 10D, 20 D, 30 D, 35 D, or 40 D less than a Shore durometer of the hard filament.

The system 100 may be configured to provide a jacket 118 between the Shore durometers of a hard filament and a soft filament. In some embodiments, the filament handling system 106 may provide a hard filament having a Shore durometer equal to 72 D and a soft filament having a Shore durometer equal to 35 D. The system 100 may be capable of providing a jacket 118 having a Shore durometer that is equal to or greater than 35 D and less than or equal to 72 D.

The system 100 may be configured to provide a jacket 118 having, or defining, segments with different Shore durometers. In some embodiments, the system 100 may be capable of providing a jacket 118 having one or more of a 35 D segment, a 40 D segment, 55 D segment, and a 72 D segment.

The filaments 114 may have any suitable width or diameter. In some embodiments, the filaments 114 have a width or diameter of 1.75 mm. In some embodiments, the filaments 114 have a width or diameter of less than or equal to 1.75, 1.5, 1.25, 1, 0.75, or 0.5 mm.

Segments may have uniform or non-uniform Shore durometers. The system 100 may be configured to provide jacket 118 having one or more segments with non-uniform Shore durometers. In some embodiments, the jacket 118 may include continuous transitions between at least two different Shore durometers, for example, as shown in FIG. 6.

The controller 110 may be configured to change a feeding force applied to one or more of the filaments 114 to change a ratio of material in the jacket over a longitudinal distance. By varying the feeding force, the system 100 may provide different Shore durometer segments in a jacket 118, whether uniform or non-uniform. In one example, sharp transitions between uniform segments may be provided by stopping or slowing longitudinal movement while continuously, or discretely with a large step, changing the feeding force of one filament relative to another filament of the substrate 116 relative to the heating cartridge 102. In another example, gradual transitions between segments may be provided by continuously, or discretely with small steps, changing the feeding force of one filament relative to another filament while longitudinally moving the substrate 116 relative to the heating cartridge 102.

The one or more wires 115 provided by the wire handling system 107 may be introduced in any suitable manner. In some embodiments, the wires 115 may be attached to the substrate 116 and pulled by movement of the substrate. One example of a wire is a pull wire that may be used to steer the catheter produced by the system 100. In some embodiments, a particularly shaped heating cartridge may be used to accommodate one or more wires 115.

Any suitable type of heating element 104 may be used. In some embodiments, the heating element 104 may be a resistive-type heating element, which may provide heat in response to an electrical current. Other types of heating elements that may be used for the heating element 104 include a radio frequency (RF) or ultrasonic-type heating element. The heating element 104 may be capable of providing heat sufficient to melt the filaments 114. In some embodiments, the heating element 104 may heat the filaments 114 to greater than or equal to 235, 240, 250, or 260 degrees Celsius. In general, the one or more heating elements 104 may be used to heat the filaments 114 to any suitable melting temperature known to one of ordinary skill in the art having the benefit of this disclosure.

Figure 2:
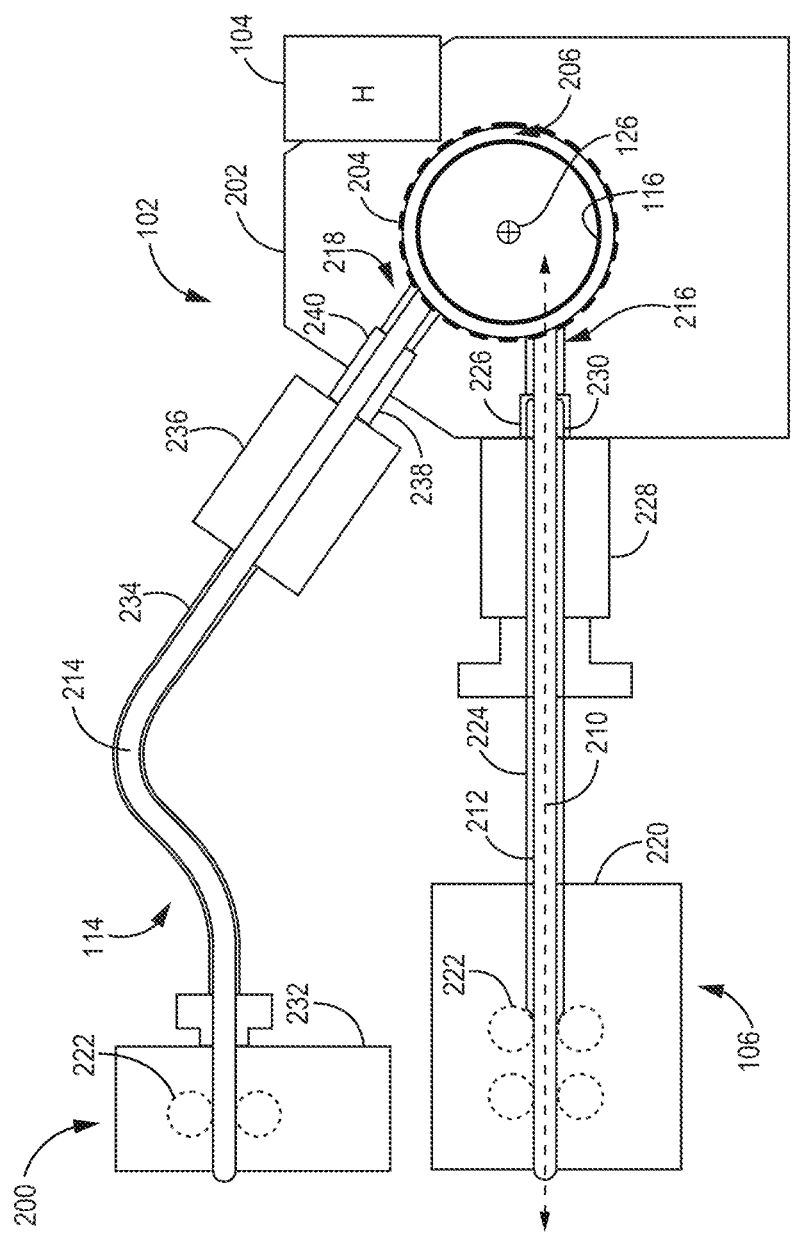
FIG. 2 is a conceptual diagram of an illustrative additive manufacturing apparatus for use with, for example, the additive manufacturing system of FIG. 1.

FIG. 2 shows one example of an additive manufacturing apparatus 200 of the additive manufacturing system 100 in an end view along the longitudinal axis 126, which is illustrated as a circle and cross. More detail of some components of the additive manufacturing system 100 are shown, such as the heating cartridge 102 and the filament handling system 106.

The heating cartridge 102 may include a heating block 202 at least partially defining an interior volume 204. The interior volume 204 may be heated by the heating element 104. The heating element 104 may be thermally coupled to the heating block 202 to melt filament material in the interior volume 204. In general, the system 100 may be configured to melt any portion of the filaments 114 in the interior volume 204. The heating element 104 may be disposed in an exposed or exterior volume defined in the heating block 202. The heating element 104 may be positioned proximate to or adjacent to the interior volume 204. In some embodiments, one, two, three, or more heating elements 104 may be thermally coupled to the heating block 202.

The heating block 202 may allow the substrate 116, which may be an elongate substrate or member, to pass through the heating block. The substrate 116 may be able to extend, or pass, through the interior volume 204. The substrate channel 206 defined by the heating cartridge 102 may extend through the interior volume 204. The substrate channel 206 may extend in a same or similar direction as the substrate 116. The substrate channel 206 may extend along the longitudinal axis 126.

A width or diameter of the interior volume 204 is larger than a width or diameter of the substrate 116. The width or diameter of the interior volume 204 or the substrate 116 is defined in a lateral direction, which may be orthogonal to the longitudinal axis 126. In one example, the lateral direction may be defined along a lateral axis 210. In some embodiments, the clearance between the substrate 116 and interior volume 204 is relatively small to facilitate changes in composition of filament material used to form the jacket 118 (FIG. 1) around the substrate 116.

The portion of the interior volume 204 around the substrate 116 may receive a flow of melted filament material from the filaments 114. When more than one filament material is provided to the interior volume 204, the filament materials may flow and blend, or mix, around the substrate 116.

In the illustrated embodiment, the filaments 114 includes a first filament 212 and a second filament 214. The first filament 212 may be provided into the interior volume 204 through a first filament port 216 at least partially defined by the heating block 202. The second filament 214 may be provided into the interior volume 204 through a second filament port 218 at least partially defined by the heating block 202. Each filament port 216, 218 may be at least partially defined by the heating block 202. Each filament port 216, 218 may be in fluid communication with the interior volume 204.

The filaments 114 may be delivered to the interior volume 204 in the same or different manners. In the illustrated embodiment, the first filament 212 is delivered to the interior volume 204 in a different manner than the second filament 214.

The filament handling system 106 may include a first handling subassembly 220. The first handling subassembly 220 may deliver the first filament 212 to the interior volume 204. The first handling subassembly 220 may include one or more pinch rollers 222. Each of the one or more pinch rollers 222 may be operably coupled to a motor. Any suitable number of pinch rollers 222 may be used. As illustrated, the first handling subassembly 220 may include two sets of pinch rollers 222. Pinch rollers 222 may be used to apply a motive force to the first filament 212 to move the first filament, for example, toward the interior volume 204.

The heating cartridge 102 may include a first guide sheath 224. The first guide sheath 224 may extend between the filament handling system 106 and the interior volume 204. The first guide sheath 224 may be coupled to the heating block 202. The first guide sheath 224 may extend into the first filament port 216 from an exterior of the heating block 202. The first guide sheath 224 may define a lumen in fluid communication with the interior volume 204. An inner width or diameter of the lumen may be defined to be greater than a width or diameter of the first filament 212. The first filament 212 may extend through the first guide sheath 224 from the pinch rollers 222 of the first handling subassembly 220 to the first filament port 216 and extend distally past the first guide sheath 224 into the interior volume 204.

As used herein with respect to the filaments 114, the term "distal" refers to a direction closer to the interior volume 204 and the term "proximal" refers to a direction closer to the filament handling system 106.

In some embodiments, a proximal end of the first guide sheath 224 may terminate proximate to one of the pinch rollers 222. A distal end of the first guide sheath 224 may terminate at a shoulder 226 defined by the first filament port 216. A distal portion or distal end of the first guide sheath 224 may be positioned proximate to or adjacent to the interior volume 204.

The inner width or diameter of the lumen of the first guide sheath 224 may be defined to be substantially the same or equal to an inner width or diameter of the first filament port 216, such as a smallest inner width or diameter of the first filament port. In other words, an inner surface of the first guide sheath 224 may be flush with an inner surface of the first filament port 216.

In some embodiments, the heating cartridge 102 may include a support element 228. The support element 228 may be coupled to the first guide sheath 224. The first guide sheath 224 may extend through a lumen defined by the support element 228. The support element 228 may be proximate to the heating block 202. In the illustrated embodiment, the support element 228 is coupled to the heating block 202. The support element 228 may include a coupling protrusion configured to be mechanically coupled to a coupling receptacle 230 defined by the first filament port 216. In some embodiments, the coupling receptacle 230 may define threads and the coupling protrusion of the support element 228 may define complementary threads.

The coupling receptacle 230 may terminate at the shoulder 226 of the first filament port 216. The coupling protrusion of the support element 228 may be designed to terminate at the shoulder 226. In some embodiments, a distal end of the support element 228 and the distal end of the first guide sheath 224 may engage the shoulder 226. In other embodiments, the distal end of the support element 228 may engage the shoulder 226 and the distal end of the first guide sheath 224 may engage a second shoulder (not shown) defined by the first filament port 216 distal to the shoulder 226.

When the first filament port 216 defines one shoulder, the first filament port 216 may define at least two different inner widths or diameters. The larger inner width or diameter may be sized to thread the support element 228 and the smaller inner width or diameter may be sized to match the inner width or diameter of the first guide sheath 224.

When the second filament port 218 defines two shoulders, the first filament port 216 may define at least three different inner widths or diameters. The largest inner width or diameter may be sized to thread the support element 228. The intermediate inner width or diameter may be sized to receive a distal portion of the first guide sheath 224. The smallest inner width or diameter may be sized to match the inner width or diameter of the first guide sheath 224.

The filament handling system 106 may include a second handling subassembly 232. The second handling subassembly 232 may deliver the second filament 214 to the interior volume 204. The second handling subassembly 232 may include one or more pinch rollers 222. Each of the one or more pinch rollers 222 may be operably coupled to a motor. Any suitable number of pinch rollers 222 may be used. As illustrated, the second handling subassembly 232 may include one set of pinch rollers 222. Pinch rollers 222 may be used to apply a motive force to the second filament 214.

The heating cartridge 102 may include one or more of a second guide sheath 234, a heat sink 236, and a heat break 238. The second guide sheath 234 may extend at least between the second handling subassembly 232 and the heat sink 236. The second guide sheath 234 may be coupled to the heat sink. The second guide sheath 234 may be coupled to the second handling subassembly 232. The heat sink 236 may be coupled to the heat break 238. The heat break 238 may be coupled to the heat block 202. The heat break 238 may extend into the second filament port 218 from an exterior of the heating block 202.

The second guide sheath 234 may define a lumen in fluid communication with the interior volume 204. The second filament 214 may extend through the second guide sheath 234 from the second handling subassembly 232 to the heat sink 236, through the heat sink 236, through the heat break, and through the second filament port 218. In some embodiments, the second guide sheath 234 may extend to the pinch rollers 22 in the second handling subassembly 232. In some embodiments, the second guide sheath 234 may extend at least partially into the heat sink 236.

The heat break 238 may be proximate to the heating block 202. The heat break 238 may be positioned between the heat sink 236 and the heating block 202. The heat break 238 may include a coupling protrusion configured to mechanically couple to a coupling receptacle 240 defined by the second filament port 218. In some embodiments, the coupling receptacle 240 may define threads and the coupling protrusion of the heat break 238 may define complementary threads. The second filament port 218 may include one or more shoulders such as those described with respect to the first filament port 216, except that the second filament port 218 may not be configured to receive the second guide sheath 234. The inner width or diameter of the support element 228 may be larger than the inner width or diameter of the heat break 238, for example, to accommodate the outer width or diameter of the first guide sheath 224. In other embodiments, the second filament port 218 may be configured to receive the second guide sheath 234 in a similar manner to the first filament port 216 receiving the first guide sheath 224.

Any suitable material may be used to make the guide sheaths 224, 234. In some embodiments, one or both guide sheaths 224, 234 may include a synthetic fluoropolymer. One or both guide sheaths 224, 234 may include polytetrafluoroethylene (PTFE). Another suitable material may include an ultra-high molecular weight polyethylene (UHMWPE).

Any suitable material may be used to make the support element 228. In some embodiments, the support element 228 may be a thermal insulator. The support element 228 may include a thermoplastic. The support element 228 may be made of a polyamide-imide, such as a TORLON polyamide-imide (commercially available from McMaster-Carr Supply Co. of Elmhurst, Ill.). Other suitable materials may include liquid-crystal polymer, polyaryletherketone (PAEK), polyphenylene sulfide, and polysulfone.

The support element 228 may provide mechanical support to the first guide sheath 224. The support element 228 may include a substantially rigid material. In some embodiments, the support element 228 include a material having a higher durometer than material used to make the first guide sheath 224.

Any suitable material may be used to make the heat sink 236. The heat sink 236 may include a high thermal conductivity material. In some embodiments, the heat sink 236 includes aluminum.

Any suitable material may be used to make the heat break 238. The heat break 238 may include a low thermal conductivity material. In some embodiments, the heat break 238 includes titanium. The heat break 238 may include a necked portion to reduce the amount of material between a proximal portion and a distal portion of the heat break. The necked portion may facilitate a reduced thermal conductivity between the proximal portion and the distal portion of the heat break 238.

In general, use of the apparatus 200 may facilitate using softer filaments at high feed forces and pressures, which tend to compress the soft filament and may result in jamming. Using higher feed forces and pressures may allow for a greater range of process conditions and may provide a consistent jacket around the substrate. In particular, use of the first guide sheath 224 extending at least partially into the first filament port 216 may facilitate the use of softer filament and greater "push-ability." Additionally, or alternatively, the use of the support element 228 may also facilitate the use of softer filament and greater "push-ability." In other embodiments, the apparatus 200 may include a screw or static mixer to help push a softer filament. In other words, the screw or static mixer may provide a cavity for softer filament material to be moved forward between the threads of the screw.

Figure 3:
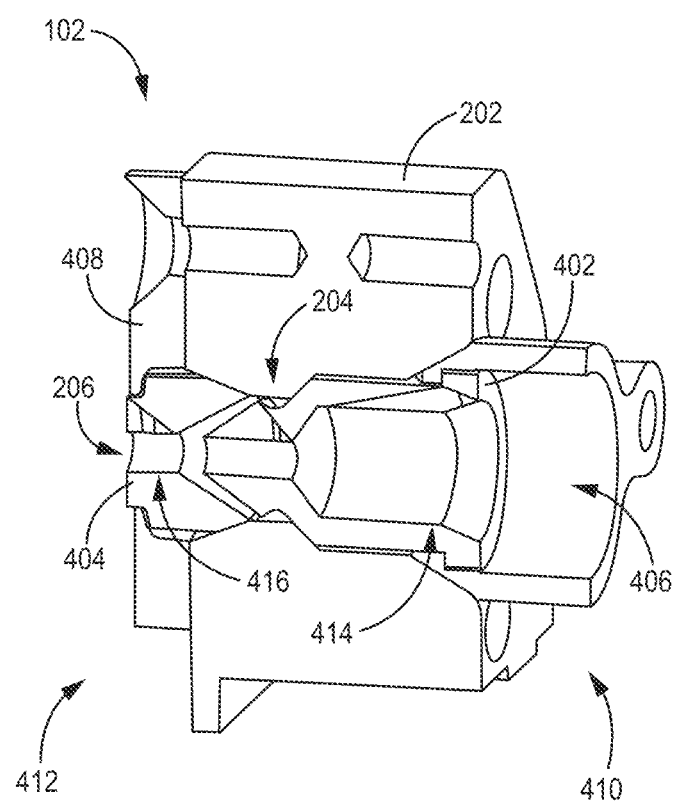
FIG. 3 is a conceptual diagram of an illustrative heating cartridge for use with, for example, the additive manufacturing system of FIG. 1.

FIG. 3 shows a partial cross-sectional side view of one example of the heating cartridge 102. The heating cartridge 102 or the heating block 202 may extend from a proximal side 410 to a distal side 412. In some embodiments, the heating cartridge 102 may include one or more of the heating block 202, an inlet die 402 coupled to the proximal side 410 of the heating block, an outlet die 404 coupled to the distal side 412 of the heating block, a proximal retaining plate 406 to facilitate retaining the inlet die adjacent to the heating block, and a distal retaining plate 408 to facilitate retaining the outlet die adjacent to the heating block.

The inlet die 402 and the outlet die 404 may be retained in any suitable manner. In the illustrated embodiment, the outlet die 404 may be retained by a distal shoulder of the distal retaining plate 408. In some embodiments, the inlet die 402 may be retained by the proximal retaining plate 406 between a distal shoulder of the proximal retaining plate 406 and a fastener, such as a nut with a lumen extending through, which may be threaded to the retaining plate to engage a proximal surface of the inlet die. The retaining plates 406, 408 may be fastened to the heating block 202 in any suitable manner.

The inlet die 402 may at least partially define a substrate inlet port 414. The outlet die 404 may at least partially define a substrate outlet port 416. The inlet die 402 may at least partially define the interior volume 204. The outlet die 404 may at least partially define the interior volume 204. In some embodiments, an exterior surface of the inlet die 402, an interior surface of the outlet die 404, and an interior surface of the heating block 202 may cooperatively define the interior volume 204.

The substrate channel 206 may be described as extending from the proximal side 410 to the distal side 412 of the heating cartridge 102, or vice versa. The substrate channel 206 may extend through the interior volume 204. As shown, the substrate channel 206 may extend through one or more of the proximal retaining plate 406, the inlet die 402, the heating block 202, the outlet die 404, and the distal retaining plate 408.

Figure 4:
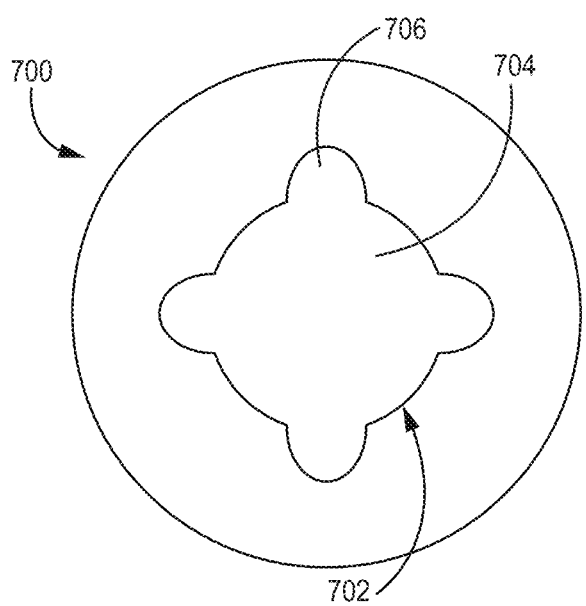
FIG. 4 is a conceptual diagram of an illustrative outlet die that may be used, for example, in the heating cartridge in the additive manufacturing system of FIG. 1.

FIG. 4 shows an end view of one example of an inlet or outlet die 700 that may be used in the heating cartridge 102 (FIG. 1). The die 700 may define a substrate inlet or outlet port 702. The port 702 may define a main region 704 and one, two, three, four, or more cutouts 706, or cutout regions. In the illustrated embodiment, the port 702 defines four cutouts 706.

When the interior cross-sectional shape die 700 is used in an outlet die, the jacket formed by the heating cartridge 102 may include a number of protrusions corresponding to the number of cutouts 706 used in the die 700. For example, the illustrated die 700 would produce four protrusions on the jacket.

In some embodiments, one or more of the cutouts 706 may be sized to receive a wire 115 (FIG. 1), such as a pull wire, which may be provided by the wire handling system 107 (FIG. 1). In some embodiments, the interior cross-sectional shape of die 700 may be used in both the input die and the outlet die to accommodate the wires 115 pulled through the cutouts 706.

Figure 5:
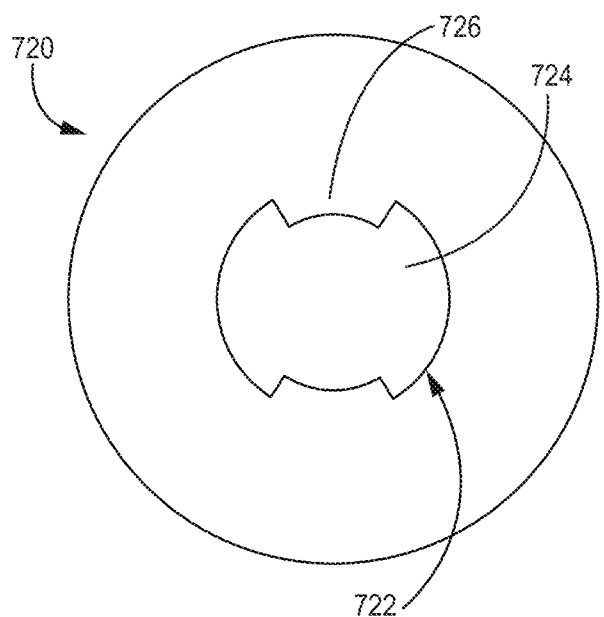
FIG. 5 is a conceptual diagram of another illustrative outlet die that may be used, for example, in the heating cartridge in the additive manufacturing system of FIG. 1.

FIG. 5 shows an end view one example of an inlet or outlet die 720 that may be used in the heating cartridge 102 (FIG. 1). The die 720 may define a substrate inlet or outlet port 722. The port 722 may define a main region 724 and one, two, three, four, or more protrusions 726, or cutout regions. In the illustrated embodiment, the port 722 defines two protrusions 726, or teeth.

When the interior cross-sectional shape die 720 is used in an outlet die, the jacket formed by the heating cartridge 102 may include a number of channels corresponding to the number of protrusions 726 used in the die 720. For example, the illustrated die 720 would produce two channels on the jacket.

The shape and feature of the outlet die 720 may control the shape and features of a resultant first jacket 500. For example, as shown in FIG. 6, the first jacket 500 defines cutouts 504 in the outer surface 502 of the first jacket 500. The first jacket 500 may be similar to the jacket 118 described herein, but may be the initial jacket that is formed and may include geometrical features thereon (e.g., the cutouts 504) upon which a second jacket may be subsequently formed. The cutouts 504 may be a result of the corresponding outlet die through which the first jacket 500 was formed. For example, the first jacket 500 of FIG. 6 defines four symmetrical cutouts having a partially circular shape. Therefore, the outlet die through which the first jacket 500 was formed included four symmetrical protrusions that are semi-circular and extend towards the center of the opening of the outlet die. Further, the cutouts 504 may extend along and parallel to the longitudinal axis 126 or may spiral or corkscrew around the outer surface 502 of the first jacket 500. While FIG. 6 illustrates four symmetrical cutouts 504, the features defined within the first jacket 500 may be any suitable shape and/or size.

After forming the first jacket 500 including features as shown in FIG. 6, one or more internal components (e.g., a lumen, a pull wire, a liner, etc.) may be deposited on the first jacket 500 (e.g., within the features defined in the first jacket 500). For example, the internal components may be positioned within channels, between protrusions, or within protrusions formed in the first jacket. A pull wire 115 may be provided by the wire handling system 107 (e.g., as shown in FIG. 1) and positioned within the cutout 504. Specifically, the number of pull wires may correspond to the number of internal components formed on the first jacket 500. As shown in FIG. 6, there may be four pull wires positioned in the first jacket 500 (e.g., one pull wire in each cutout 504). By positioning the pull wires within the pre-formed cutouts 504, the pull wires may be more effectively and consistently spaced apart.

Thereafter, a second jacket may be formed around the first jacket 500 and any internal components positioned therein. The second jacket may be formed similar to the first jacket 500 (or, e.g., as described herein as it pertains to the jacket 118) such as by feeding a second filament into the interior cavity of the heating cartridge, melting the second filament within the interior cavity, and moving the heating cartridge to form the second jacket. Further, the second jacket may be formed using the same heating cartridge as the first jacket or a different heating cartridge.

For example, in one or more embodiments, the heating cartridge 102 of the system 100 (e.g., as shown in FIG. 1) may make multiple passes (e.g., two) along the substrate to form each of the first and second jackets. Once the heating cartridge 102 extends the length of the substrate 116 to form the desired length first jacket 500, the heating cartridge 102 may return to the starting position and begin forming the second jacket. In other words, a first filament may be fed into and melted within the interior cavity of the heating cartridge 102 to form the first jacket and a second filament may be fed into and melted within the interior cavity of the same heating cartridge 102 to form the second jacket. In such embodiments, the first and second filaments may be the same filament being fed into the heating cartridge 102 (e.g., if the heating cartridge 102 only includes a single filament port). Although in some embodiments, as described herein, the heating cartridge 102 may include at least two filament ports. Therefore, the first jacket may be formed from a first filament and the second jacket may be formed from a second filament different than the first filament. In one or more embodiments, the first and second jackets may be formed from any combination of both the first and second filaments.

Figure 7:
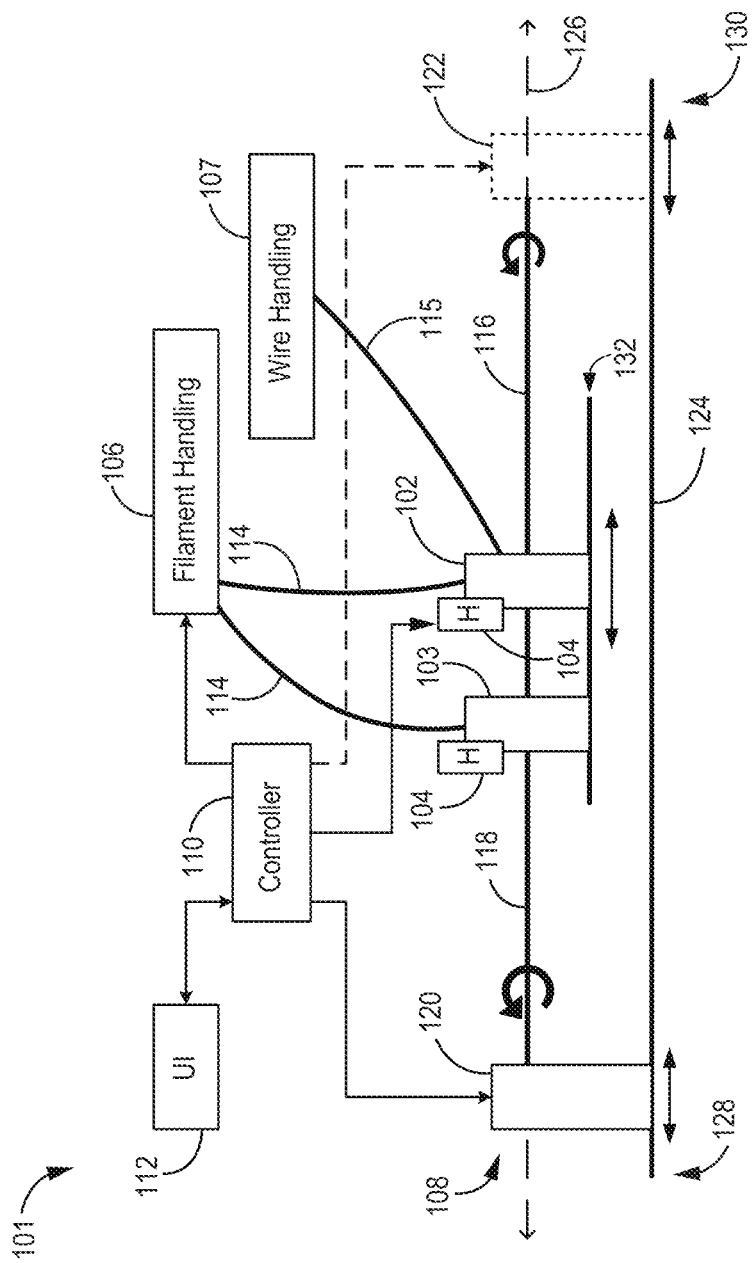
FIG. 7 is a conceptual diagram of another illustrative additive manufacturing system according to the present disclosure.

Also, as shown in FIG. 7, the system 101 may include an additional heating cartridge 103 that is distal to or trailing the heating cartridge 102. Specifically, the additional heating cartridge 103 may be longitudinally spaced (e.g., along the longitudinal axis 126) apart from the heating cartridge 102. The system 101 may include all of the same components as system 100 described in combination with FIG. 1, but include the additional heating cartridge 103. Further, the additional heating cartridge 103 may include all of the same features as the heating cartridge 102, but may be physically separate from the heating cartridge 102. In such embodiments, the heating cartridge 102 may form the first jacket and the additional heating cartridge 103 may subsequently form the second jacket around the first jacket. For example, the heating cartridge 102 may define a first filament port in fluid communication with the interior volume to receive the first filament and the additional heating cartridge 103 may define a second filament port in fluid communication with the interior volume of the additional heating cartridge to receive the second filament.

Even though the heating cartridges are separate components, the first and second filament may include a same or different filament material. Further, each of the heating cartridge 102 and the additional heating cartridge 103 may include two or more filament ports such that the jacket may be formed from a mixture of materials. As described herein, by combining filament materials into a single jacket, the characteristics (e.g., the flexibility) of the jacket may be customized. The one or more pull wires located within the catheter (e.g., between the first and second jacket) may produce varying types of movement of the catheter depending on the characteristics of the material mixture of the first and second jackets. For example, if the second jacket (e.g., outer jacket) is stiffer than the first jacket (e.g., inner jacket), the pull wires may provide greater range of motion.

As shown in each of FIGS. 1 and 7, the wire handling system 107 (which may include the one or more pull wires) may feed the pull wires 115 through the heating cartridge 102 to be positioned along the catheter. When the system 100 (e.g., as shown in FIG. 1) includes a single heating cartridge 102 making multiple passes, the pull wire 115 may be positioned after the first jacket is formed and prior to the second jacket being formed. When the system 101 (e.g., as shown in FIG. 7) includes a heating cartridge 102 and an additional heating cartridge 103, the pull wire 115 may be configured to be positioned between the heating cartridge 102 and the additional heating cartridge 103 (e.g., between the formation of the first and second jackets).

Figure 8:
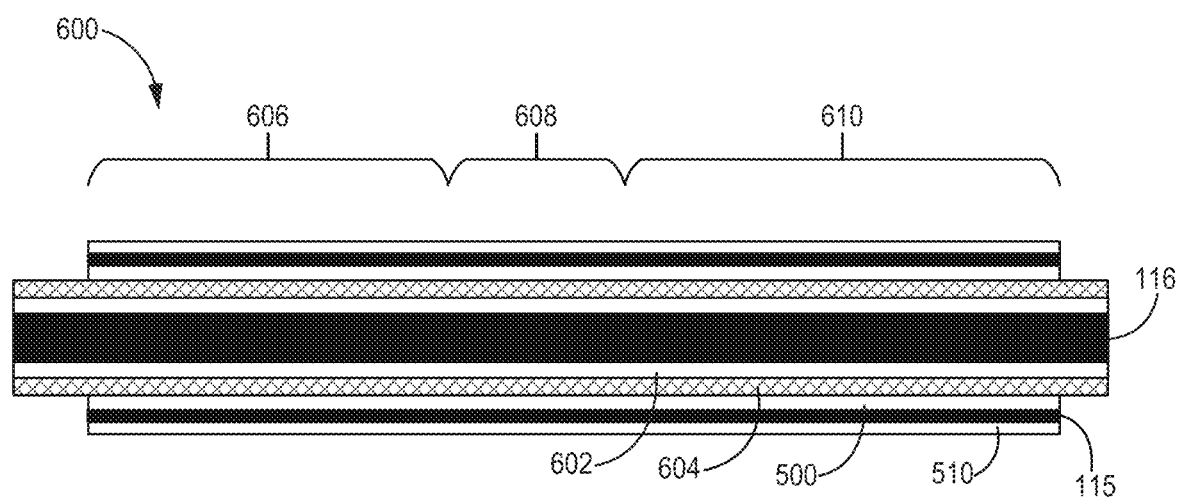
FIG. 8 is a conceptual diagram of the illustrative catheter jacket of FIG. 6 including pull wires and a second jacket using the additive manufacturing system described herein.

FIG. 8 shows one example of a catheter 600 that may be manufactured using the system 100 before the substrate 116 is removed. The substrate 116 may include a lubricious coating on its exterior surface to facilitate removal. The lubricious coating may extend around the circumference of the substrate 116. One example of a lubricious coating is a PTFE coating.

The substrate 116 may be covered with a liner 602, such as a PTFE layer. The liner 602 may be placed over the lubricious coating. The liner 602 may extend around the circumference of the substrate 116.

The liner 602 may be covered with a braid 604, such as a stainless-steel braid layer. The braid 604 may be placed over the liner 602. The braid 604 may extend around the circumference of the liner 602. The braid 604 may be porous.

The first jacket 500 may be applied to the braid 604. When the first jacket 500 is formed, the liner 602 may adhere to the first jacket 500 through pores in the braid 604.

As described herein the first jacket 500 may be formed with one or more cutouts (e.g., see FIG. 6). As shown in FIG. 8, the cutouts are filled with pull wires 115 extending along the length of the catheter 600.

Thereafter, the second jacket 510 may be formed around the first jacket 500 and the pull wires 115.

In the illustrated embodiments, the catheter 600 includes a first segment 606, a second segment 608, and a third segment 610. Each segment 606, 608, 610 may have different durometers. In some embodiments, the first segment 606 may have a high durometer, the third segment 610 may have a low durometer, and the second segment 608 may have a continuously varying durometer in a longitudinal direction between the durometers of the first and third segments. For example, the first segment 606 may have a Shore durometer equal to 72 D, the third segment 610 may have a Shore durometer equal to 35 D, and the second segment 608 may have a Shore durometer that gradually changes from 72 D to 35 D over its length. Further, the first and second jackets 500, 510 may have the same or differing profiles extending along the longitudinal direction.

Figure 9:
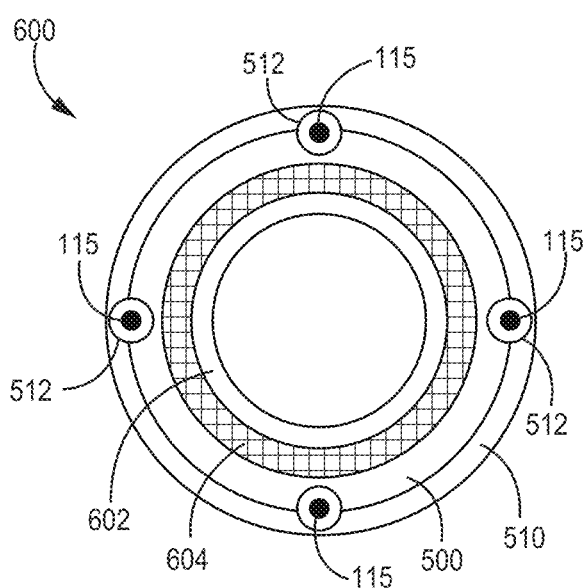
FIG. 9 is cross-sectional conceptual diagram of the illustrative catheter of FIG. 8.

FIG. 9 illustrates the catheter 600 of FIG. 8 from the conceptual cross-sectional view and without the substrate 116 positioned therein. As described herein, the first jacket 500 is formed around the braid 604 and the liner 602. The pull wires 115 are positioned within a portion of the first jacket 500 and surrounded by a liner 512 (e.g., a PTFE pull wire liner). The second jacket 510 may be formed around the first jacket 500 and the pull wire liners 512. The pull wires 115 may be symmetrically positioned around and embedded in the catheter 600. The process of embedding internal components as described herein may assist in easily spacing those internal components in a concentric way that may benefit mechanical properties and physician handling (e.g., moving the pull wires).

Figure 10:
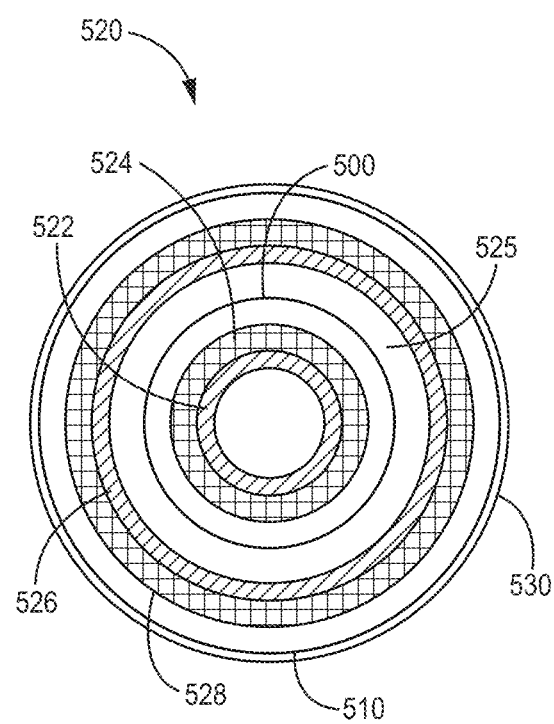
FIG. 10 is a cross-sectional conceptual diagram of another illustrative catheter that may be manufactured using the additive manufacturing system of FIG. 1.

Furthermore, other types of medical devices may be formed using the multiple jacket processes described herein. For example, FIG. 10 illustrates a cross-sectional view of a balloon catheter 520 defining an empty space lumen 525 as an internal component. Specifically, the catheter 520 may include a first liner 522 extending around the substrate (not shown). A first braid 524 may be positioned around the first liner 522 and a first jacket 500 may be formed on the first braid 524.

Next, a second liner 526 may be positioned to include an empty space 525 between the first jacket 500 and the second liner 526. In one or more embodiments, the first jacket 500 may include surface features (e.g., bumps, grooves, channels, etc.) such that the second liner 526 does not completely enclose the empty space 525. In other words, the surface features on the first jacket 500 may support the second jacket 510 above the first jacket 500. Further, in one or more embodiments, the materials of the first jacket 500 and the second liner 526 (or, e.g., the second jacket 510 formed thereon) may be selected such that the materials may repel (e.g., not fuse together) and separate when a fluid flows into the empty space 525.

In one or more embodiments, a second braid 528 may surround the second liner 526 and the second jacket 510 may be formed thereon. Further, a balloon 530 may surround the second jacket. Therefore, the empty space 525 may be used as a fluid channel or gap to inflate the balloon 530 using, e.g., air or saline.

Figure 11:
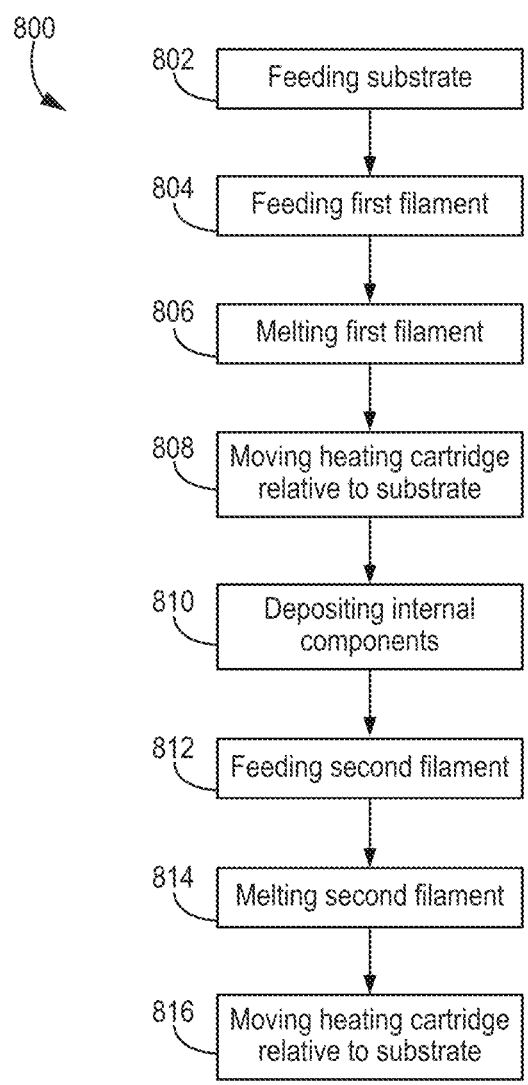
FIG. 11 is a flow diagram that illustrates one example of a method for use with, for example, the additive manufacturing system of FIG. 1.

FIG. 11 shows one example of a method 800 of using the systems 100, 101 (FIGS. 1 and 7) for additive manufacturing. The method 800 may be used to manufacture an implantable medical device.

The method 800 may include feeding the substrate 802, for example, through a substrate channel in one or more heating cartridges. The substrate channel may be in fluid communication with an interior cavity of the heating cartridge.

The method 800 may include feeding at least a first filament 804 through a filament port of the heating cartridge into the interior cavity.

The method 800 may include melting the first filament 806, for example, in the interior cavity. Any portion of the filaments contained in the interior cavity may be melted.

The method 800 may include moving the heating cartridge relative to the substrate 808, for example, at least in a longitudinal direction to form a first jacket comprising material from at least the first filament. The heating cartridge or substrate may also be rotated relative to one another. The jacket may be formed from material of at least the first filament. In some embodiments, the jacket may be formed from material of at least the first filament and the second filament. In one or more embodiments, the outlet die may form various surface features within the outer surface of the first jacket.

For example, in one or more embodiments, forming the first jacket may include defining one or more protrusions extending from an outer surface of the first jacket. In one or more embodiments, forming the first jacket may include defining one or more channels or cutouts extending inward from an outer surface of the first jacket.

The method 800 may also include depositing one or more internal components 810 on the first jacket (e.g., relative to the features formed on the surface of the first jacket). For example, the one or more components may be deposited between the one or more protrusions or within the one or more channels.

The method 800 may include feeding at least a second filament 812 through a filament port of the heating cartridge into the interior cavity and melting the second filament 814 in the interior cavity of the one or more heating cartridges. The method 800 may include moving the heating cartridge relative to the substrate 816, for example, at least in a longitudinal direction to form a second jacket comprising material from at least the second filament. The heating cartridge or substrate may also be rotated relative to one another. The jacket may be formed from material of at least the second filament. In some embodiments, the jacket may be formed from material of at least the first filament and the second filament.

As described herein, the first and second jackets may be formed by a single heating cartridge making multiple passes along the substrate or by two separate heating cartridges that are spaced apart from one another.

Additionally, the present disclosure generally provides additive manufacturing systems and methods for medical devices, such as catheters, that allows for providing a lumen extending through the medical device with a non-circular cross-sectional shape. For example, two or more elongate substrates may be arranged relative to one another to define the shape of the lumen and the catheter jacket may be printed thereon. This concept allows for specialty shapes through the full length of the catheter, and may allow for new technologies and advancements in catheter research Traditional catheters often use a cylindrical lumen or circular cross-section inside the catheter body and designs that require non-cylindrical (or non-circular cross-section) lumen features may use expensive and time-consuming tooling. For example, custom machined dies and tooling may create a "neckable" core rod (e.g., copper) that is needed to create a non-cylindrical lumen feature. Specifically, the traditional lumen design may include a neckable silicone coated ethylene tetrafluoroethylene (ETFE) wire and copper core material. The copper wire core may age harden and reduce the amount of elongation before breaking (i.e., creating a shelf life for the copper core material). Further, the traditional catheter having a non-cylindrical or non-circular lumen may require a SPCC machine to aid in core removal because as the lumen size increases, so too does the force required to remove the core from the catheter body (e.g., sizes greater than 0.08" may be extremely difficult to remove).

However, as described herein, an illustrative catheter having a non-cylindrical lumen feature may be manufactured using conventional mandrels or elongate substrates and 3D printing technologies to print a catheter jacket thereon. For example, the conventional mandrels or elongate substrates may be arranged relative to another to create a non-cylindrical lumen feature (e.g., after a catheter jacket is printed thereon and the elongate substrates are removed therefrom). The non-cylindrical or non-circular lumen feature (e.g., created from multiple mandrels or elongate substrates) may extend through the entire length of the catheter shaft. Therefore, a variety of different non-cylindrical lumen features may be created without needing special tooling to create an elongate substrate in the non-cylindrical shape.

Further, the elongate substrates that are combined to define the non-cylindrical or non-circular lumen may be independently removed to ease the removal process (e.g., compared to removing the entire core/substrate at the same time) by not requiring the use of special equipment. For example, elongate substrates having a cylindrical profile may be easier to remove than a substrate or core having a different shape profile. In other words, by using multiple substrates having a cylindrical profile to form a non-cylindrical shape, the multiple substrates may be more easily removed than a single substrate having the non-cylindrical shape. Further, the user of spacers (as described herein) may also make removal of the elongate substrates easier.

Figure 12A:
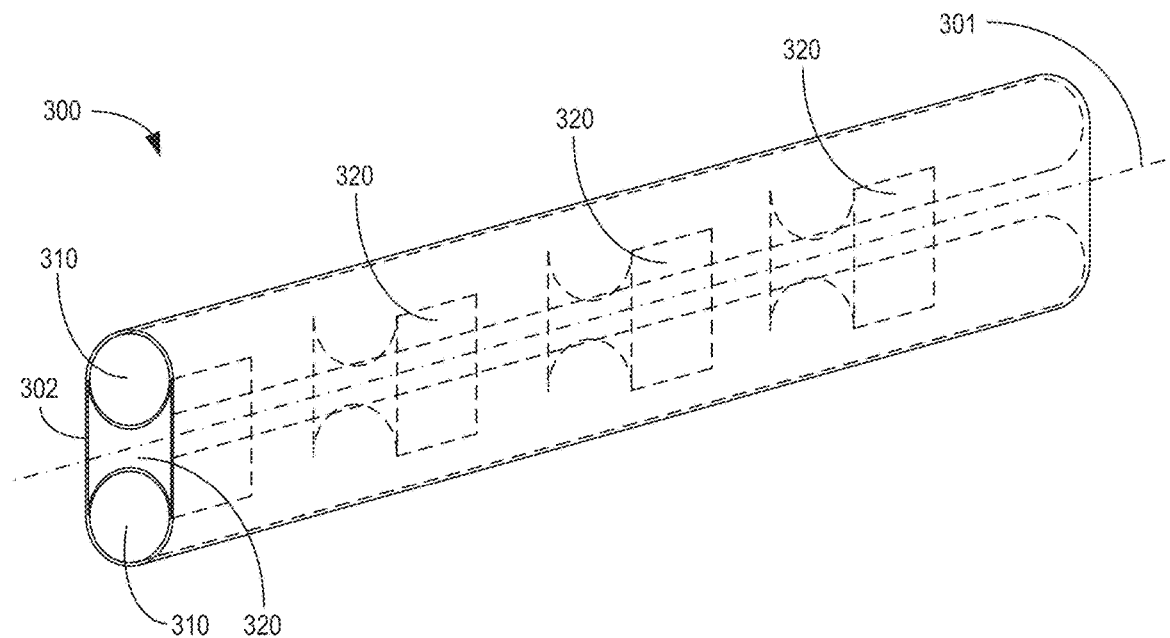
FIG. 12A is a perspective view of an illustrative catheter jacket having a non-circular lumen through the catheter jacket according to the present disclosure.

FIG. 12A illustrates one example of a catheter jacket 300 having a lumen with a non-circular cross-section and formed using additive manufacturing as described herein. For example, two or more elongate substrates 310 may be positioned relative to one another to define the profile of the lumen extending through the catheter jacket 300 created by additive manufacturing. For example, as shown in FIG. 12A, two elongate substrates 310 may be positioned relative to one another with a plurality of spacers 320 between the elongate substrates 310 to define a non-cylindrical (or non-circular cross-sectional) shape that forms the lumen. The assembly of the two elongate substrates 310 and the plurality of spacers 320 therebetween may be covered with a liner 302 (e.g., to fill any potential gaps between the elongate substrates 310 and the spacers 320).

Figure 14:
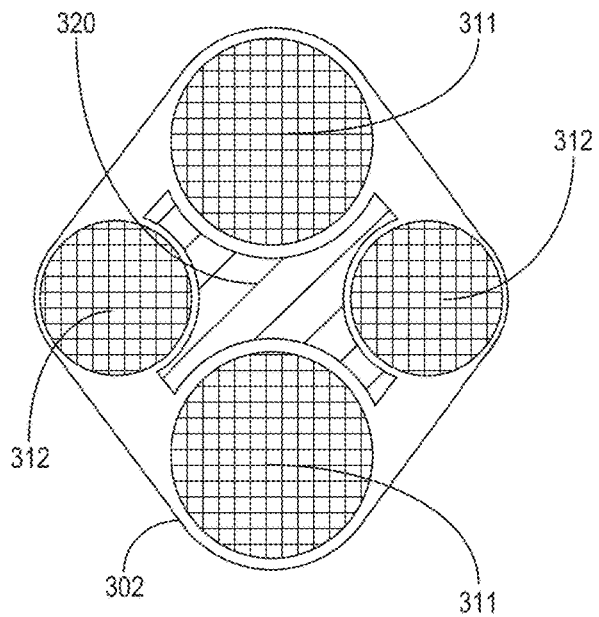
FIG. 14 is a cross-sectional view of another illustrative assembly including elongate substrates and spacers.

As described herein, the elongate substrates 310 define a cylindrical shape having a diameter and length, and may be described as mandrels or cores. The elongate substrates 310 may define any suitable size to achieve the desired lumen shape. For example, in one or more embodiments, the elongate substrates 310 may define a diameter of about 0.074". In some embodiments, the elongate substrates 310 may define a variety of different sizes that are combined to form a desired lumen profile/shape (e.g., as shown in FIG. 14). Further, the elongate substrates 310 may extend for the entire length of the catheter jacket 300 (e.g., to form a lumen extending through the entirety of the catheter). Additionally, the elongate substrates 310 may include (e.g., be formed of) any suitable materials. For example, the elongate substrates 310 may include PTFE, coated steel, 3D printed plastic, etc.

Figure 12B:
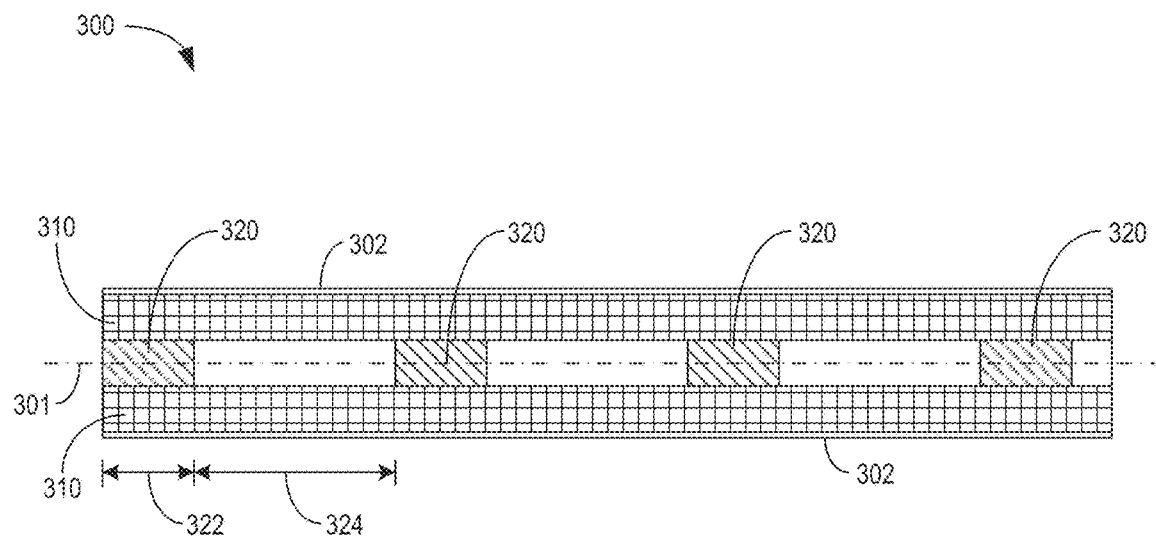
FIG. 12B is a cross-sectional view of the catheter jacket of FIG. 12A.

In one or more embodiments, the elongate substrates 310 may be spaced apart from one another by a plurality of spacers 320 (e.g., as shown in FIGS. 12A and 12B). The plurality of spacers 320 may be specifically created (e.g., using 3D printing) and sized to correspond to the arrangement of the elongate substrates 310. For example, the plurality of spacers 320 may define features (e.g., curved surfaces) that correspond to the outer surface of the elongate substrates 310 to position the elongate substrates 310 in the desired arrangement.

The plurality of spacers 320 may be spaced apart from one another along the longitudinal direction 301. For example, there may be gaps between each spacer 320. These gaps between adjacent spacers 320 may assist in removing the elongate substrates 310 after the catheter jacket 300 is printed or formed over the elongate substrates 310. For example, by providing gaps between the spacers 320, the amount of friction between the printed catheter jacket 300 and the spacers 320 (e.g., to remove the spacers 320 and the elongate substrates 310) is reduced (e.g., as compared to if the spacer extended the full length of the catheter). As such, having the plurality of spacers 320 spaced apart along the longitudinal direction 301 still assists in maintaining the proper spacing between the elongate substrates 310 while also reducing the amount of force needed to remove the elongate substrates 310 and the spacers 320. For example, in one or more embodiments, each spacer 320 may define a length 322 of about 20 mm to 40 mm (e.g., measured along the longitudinal direction 301) and may be spaced apart from adjacent spacers 320 by a distance 324 of about 1 mm to 100 mm (e.g., measured along the longitudinal direction 301). It is noted that the ratio of spacer length 322 to distance 324 between spacers 320 may vary depending on the size/shape and arrangement of the elongate substrates. For example, in some embodiments, the elongate substrates may be more supported by the spacers 320 (e.g., longer spacers 320 and/or spacers 320 closer together) or less supported by the spacers 320 (e.g., shorter spacers 320 and/or spacers 320 farther apart).

The plurality of spacers 320 may include (e.g., be formed of) any suitable material. For example, the plurality of spacers 320 may include acrylic based resin that is ultraviolet (UV) cured (e.g., through 3D printing), Form labs Rigid 10K, Form labs High Temp V2, etc. Further, the plurality of spacers 320 may be created or formed in any suitable way. For example, the plurality of spacers 320 may be created using injection molding (e.g., plastic), machining, 3D printing, metal injection molding (MIM), etc.

Furthermore, in one or more embodiments, a liner 302 may cover the elongate substrates 310 and the plurality of spacers 320. For example, the liner 302 may assist in keeping the elongate substrates 310 in the correct position relative to the spacers 320. Further, the liner 302 may provide smooth transitions between the multiple elongate substrates 310. For example, when the catheter jacket 300 is printed onto the elongate substrate 310, the filament material positioned and melted thereon may conform to the shape of the elongate substrate 310. However, the presence of the liner 302 between the elongate substrates 310 creates a smooth transition between the elongate substrates 310 (e.g., so the filament material does not print into the gaps and crevasses located between the elongate substrates 310 and spacers 320). The liner 302 may include (e.g., be formed of) any suitable material. For example, the liner 302 may include an etched PTFE material. Further, in one or more embodiments, the liner 302 may be coated with a material or substance to assist with removal of the elongate substrates 310 after the catheter jacket is printed thereon.

Figure 13A:
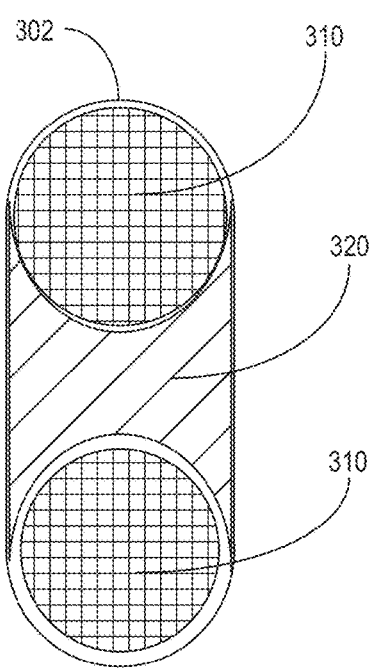
FIG. 13A is a cross-sectional view of an illustrative assembly including elongate substrates and spacers.
Figure 13B:
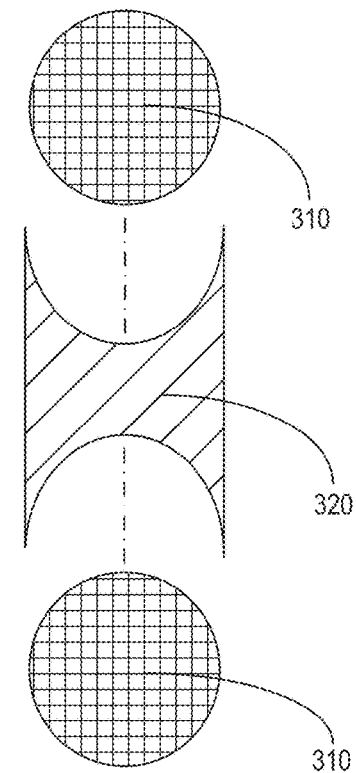
FIG. 13B is an exploded view of the assembly of FIG. 13A with elongate substrates spaced away from a spacer.
Figure 15:
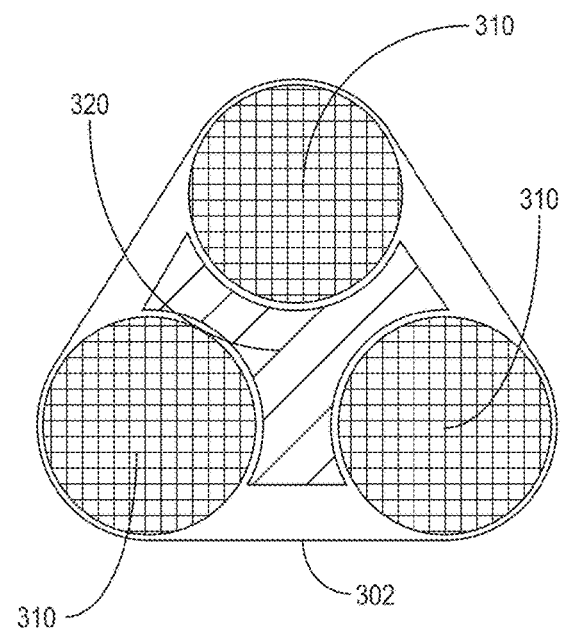
FIG. 15 is a cross-sectional view of yet another illustrative assembly including elongate substrates and spacers.

As shown in FIGS. 13A, 14, and 15, the resulting lumen formed from the elongate substrates 310 may define a variety of different shapes. For example, the two elongate substrates 310 and spacer 320 define an oblong shape in FIG. 13A. As shown in FIG. 13B, the spacer 320 defines an appropriate size and shape to receive the elongate substrates 310 on opposing sides (e.g., the spacer 320 defines cutouts that correspond to the outer surface of the elongate substrates 310). Further, as shown in FIG. 13A, a liner 302 covers and wraps around the two elongate substrates 310 and spacers 320 therebetween.

FIG. 14 illustrates two different size elongate substrates 310 arranged to define a diamond shape to form the lumen of the catheter jacket 300. For example, the elongate substrates 310 may include a first elongate substrate 311 and a second elongate substrate 312. The first elongate substrate 311 may define a cross-sectional diameter that is different than a cross-sectional diameter of the second elongate substrate 312. As shown in FIG. 14, the assembly may include two elongate substrates 310 having the first elongate substrate 311 diameter and two elongate substrates having the second elongate substrate 312 diameter. The spacer 320 is positioned between each of the elongate substrates 310.

The liner 302 covers each of the elongate substrates 310 to define a rounded diamond shape, which will form the lumen of the catheter jacket 300.

FIG. 15 illustrates three elongate substrates 310 having the same diameter and arranged relative to one another with a spacer 320 therebetween to form a rounded triangle shape. The liner 302 covers the elongate substrates to form the shape of the resulting lumen of the catheter jacket 300. It is noted that the liners 302 of FIGS. 13A, 14, and 15 are illustrated as spaced apart from the elongate substrates 310, however, the spaced apart gaps are for illustrative/viewability purposes and the liners 302 may actually be in contact and wrap around the elongate substrates 310.

Any number and size of elongate substrates 310 may be arranged to define the desired lumen shape of the catheter jacket 300. Similarly, the spacers 320 may have any suitable size and shape to define the desired lumen shape of the catheter jacket 300.

While only a few different shapes are illustrated herein, many different lumen shapes formed from two or more elongate substrates 310 is contemplated herein. For example, the two or more elongate substrates 310 may be combined to form cross-sectional shapes including oval, square, squircle, rectangle, triangle, diamond, trapezoid, parallelogram, hexagon, octagon, etc. It is noted that these shapes include variations of the shape including rounded corners.

Figure 16:
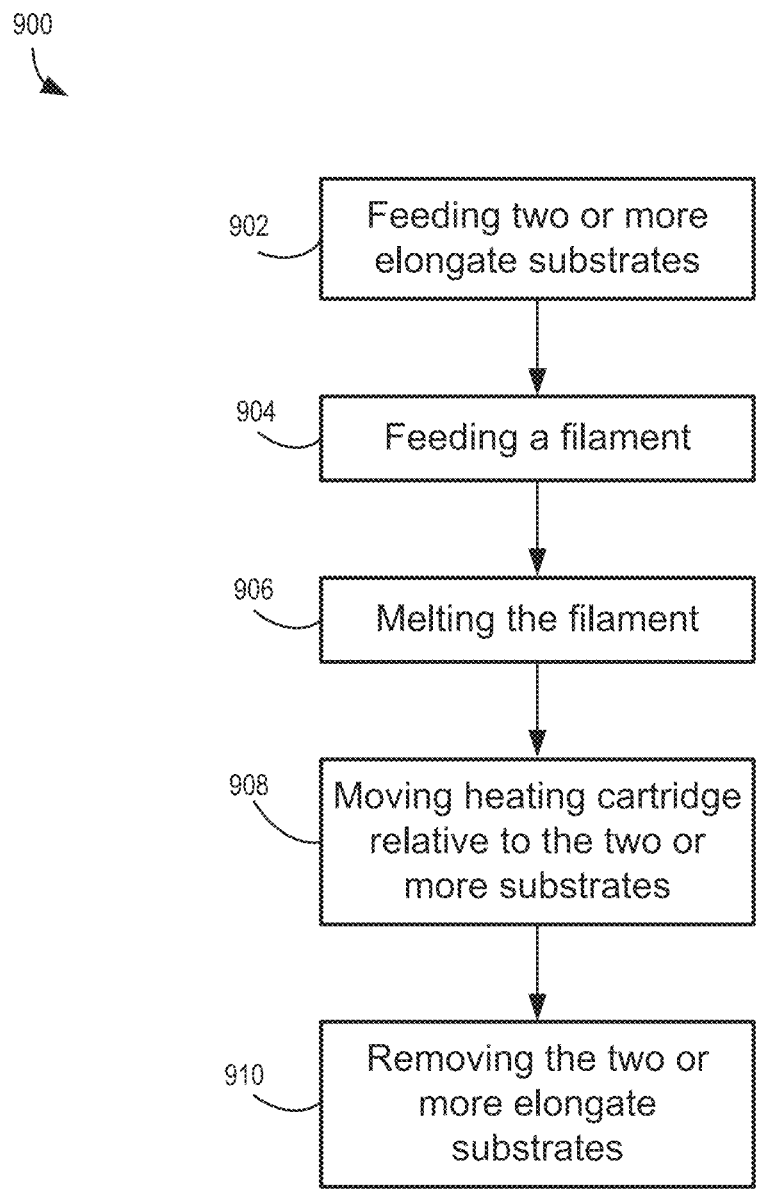
FIG. 16 is a flow diagram that illustrates one example of a method for manufacturing a catheter jacket having a non-circular lumen.

As shown in FIG. 16, the assembly having two or more elongate substrates may use a method 900 including the additive manufacturing process to define a non-cylindrical/non-circular lumen through catheter jacket formed by the additive manufacturing process. For example, the method 900 may include feeding 902 two or more elongate substrates through a substrate channel in one or more heating cartridges. The substrate channel may be in fluid communication with an interior cavity of the one or more heating cartridges. The method 900 may also include feeding 904 a filament through a filament port into the interior cavity of the one or more heating cartridges and melting 906 the filament in the interior cavity of the one or more heating cartridges. Further, the method 900 may include moving 908 the one or more heating cartridges relative to the two or more elongate substrates at least in a longitudinal direction to form a catheter jacket including material from at least the filament. Also, the method 900 may include removing 910 the two or more elongate substrates to define a non-circular lumen through the catheter jacket along the longitudinal direction.

In one or more embodiments, the method may also include inserting a plurality of spacers between the two or more elongate substrates. Each spacer of the plurality of spacers may be spaced apart from an adjacent spacer of the plurality of spacers. In one or more embodiments, the method may include covering or wrapping the two or more elongate substrates (and the spacers) with a liner prior to feeding and melting the filament.

In one or more embodiments, the method may include removing the plurality of spacers prior to removing the two or more elongate substrates. In other words, the spacers may be removed from the catheter jacket (e.g., after the catheter jacket is printed and formed) to make it easier to remove the elongate substrates.

In one or more embodiments, the two or more elongate substrates may be positioned relative to one another to define an oblong cross-sectional shape. For example, the spacers may be positioned such that the elongate substrates are arranged on either side of the spacers (e.g., on opposing sides of the spacers).

In one or more embodiments, the two or more elongate substrates may include a first elongate substrate and a second elongate substrate. The first elongate substrate may define a cross-sectional diameter that is different than a cross-sectional diameter of the second elongate substrate.

In one or more embodiments, the method may further include feeding an additional filament (e.g., a second filament) through another filament port into the interior cavity and melting the additional filament with the filament to form the catheter jacket including material from at least the first filament and the second filament. In one or more embodiments, the method may also include adjusting a ratio of the filament (e.g., a first filament) relative to the additional filament (e.g., a second filament) over a longitudinal distance to change a Shore durometer of the catheter jacket over the longitudinal distance.

ILLUSTRATIVE EMBODIMENTS

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

A1. An additive manufacturing system comprising:
  one or more heating cartridges, each extending from a proximal side to a distal side and comprising a substrate inlet port at the proximal side and a substrate outlet port at the distal side, each heating cartridge defining an interior volume and a substrate channel extending through the interior volume from the proximal side to the distal side, wherein the heating cartridge defines a first filament port in fluid communication with the interior volume to receive a first filament;
  a heating element thermally coupled to each heating cartridge of the one or more heating cartridges to heat the interior volume;
  a filament handling system comprising one or more motors to feed at least the first filament through the first filament port into the interior volume;
  a substrate handling system comprising:
    a head stock comprising a distal clamp to secure a distal portion of an elongate substrate, wherein the substrate is positioned to pass through the substrate channel when secured by the head stock; and
    one or more motors to translate or rotate one or both of the substrate when secured by the headstock and the heating cartridge relative to one another; and
  an intermediate component system positioned proximate the heating cartridge and comprising one or more internal components;
  a controller operably coupled to the heating element, one or more motors of the filament handling system, and one or more motors of the substrate handling system, the controller configured to:
    control the one or more motors of the filament handling system to selectively control the feeding of the first filament into the interior volume;
    activate the heating element to melt any portion of the first filament in the interior volume;
    control one or more motors of the substrate handling system to move one or both of the substrate and the one or more heating cartridges relative to one another in at least a longitudinal direction to form a first elongate catheter jacket around the substrate;
    control the intermediate component system to deposit the one or more internal components on the first elongate catheter jacket; and
    control the one or more motors of the filament handling system to selectively control the feeding of a second filament into the interior volume;
    activate the heating element to melt any portion of the second filament in the interior volume; and
    control one or more motors of the substrate handling system to move one or both of the substrate and the one or more heating cartridges relative to one another in at least a longitudinal direction to form a second elongate catheter jacket around the first elongate catheter jacket and the one or more internal components.

A2. The system according to embodiment A1, wherein the one or more heating cartridges comprises a first heating cartridge defining the first filament port in fluid communication with the interior volume to receive the first filament and a second filament port in fluid communication with the interior volume to receive the second filament.

A3. The system according to embodiment A2, wherein the first elongate catheter jacket comprises material from the first and second filaments.

A4. The system according to embodiments A2-A3, wherein the second elongate catheter jacket comprises material from the first and second filaments.

A5. The system according to embodiments A2-A4, wherein the intermediate component system is positioned proximate the distal side of the first heating cartridge.

A6. The system according to embodiment A2, wherein the second filament is the first filament.

A7. The system according to embodiment A1, wherein the one or more heating cartridges comprises a first heating cartridge defining the first filament port in fluid communication with the interior volume to receive the first filament and a second heating cartridge defining a second filament port in fluid communication with the interior volume of the second heating cartridge to receive the second filament, wherein the second heating cartridge is longitudinally spaced apart from the first heating cartridge and the intermediate component system is positioned therebetween.

A8. The system according to any preceding A embodiment, wherein the first and second filaments comprise a same filament material.

A9. The system according to any preceding A embodiment, wherein the first and second filaments comprise a different filament material.

A10. The system according to any preceding A embodiment, wherein the one or more internal components comprise at least one of a lumen, a pull wire, a liner, etc.

A11. The system according to any preceding A embodiment, wherein the substrate outlet port defines one or more cutouts and the first elongate catheter jacket comprises a number of protrusions corresponding to the number of cutouts, wherein the one or more internal components are deposited between the protrusions.

A12. The system according to any preceding A embodiment, wherein the substrate outlet port defines one or more protrusions and the first elongate catheter jacket comprises a number of channels corresponding to the number of cutouts, wherein the one or more internal components are deposited within the channels.

A13. The system according to any preceding A embodiment, further comprising the substrate, wherein the substrate comprises a lubricious coating, a liner, and a braid, and the catheter jacket is formed around the braid.

B1. A method for additive manufacturing of an implantable medical device, the method comprising:
   feeding a substrate through a substrate channel in one or more heating cartridges, the substrate channel in fluid communication with an interior cavity of the one or more heating cartridges;
   feeding at least a first filament through a filament port into the interior cavity of the one or more heating cartridges;
   melting the first filament in the interior cavity of the one or more heating cartridges;
   moving the one or more heating cartridges relative to the substrate at least in a longitudinal direction to form a first catheter jacket comprising material from at least the first filament;
   depositing one or more internal components on the first catheter jacket;
   feeding at least a second filament through a filament port into the interior cavity of the one or more heating cartridges;
   melting the second filament in the interior cavity of the one or more heating cartridges;
   moving the one or more heating cartridges relative to the substrate at least in the longitudinal direction to form a second catheter jacket around the first catheter jacket and the one or more internal components, wherein the second catheter jacket comprises material from at least the second filament.

B2. The method according to embodiment B1, wherein the first filament is fed into and melted within the interior cavity of a first heating cartridge of the one or more heating cartridges, and wherein the second filament is fed into and melted within the interior cavity of the first heating cartridge of the one or more heating cartridges.

B3. The method according to embodiment B2, wherein the first catheter jacket comprises material from the first and second filaments.

B4. The method according to embodiments B2-B3, wherein the second catheter jacket comprises material from the first and second filaments.

B5. The method according to embodiment B2, wherein the second filament is the first filament.

B6. The method according to embodiment B1, wherein the first filament is fed into and melted within the interior cavity of a first heating cartridge of the one or more heating cartridges, and wherein the second filament is fed into and melted within the interior cavity of a first heating cartridge of the one or more heating cartridges, wherein the second heating cartridge is longitudinal spaced apart from the first heating cartridge.

B7. The method according to any preceding B embodiment, wherein the first and second filaments comprise a same filament material.

B8. The method according to any preceding B embodiment, wherein the first and second filaments comprise a different filament material.

B9. The method according to any preceding B embodiment, wherein the one or more internal components comprise at least one of a lumen, a pull wire, a liner, etc.

B10. The method according to any preceding B embodiment, wherein forming a first catheter jacket comprises defining one or more protrusions extending from an outer surface of the first catheter jacket, wherein the one or more internal components are deposited between the one or more protrusions.

B11. The method according to any preceding B embodiment, wherein forming a first catheter jacket comprises defining one or more channels extending inward from an outer surface of the first catheter jacket, wherein the one or more internal components are deposited within the one or more channels.

C1. A method comprising:
   feeding two or more elongate substrates through a substrate channel in one or more heating cartridges, the substrate channel in fluid communication with an interior cavity of the one or more heating cartridges;
   feeding a filament through a filament port into the interior cavity of the one or more heating cartridges;
   melting the filament in the interior cavity of the one or more heating cartridges;
   moving the one or more heating cartridges relative to the two or more elongate substrates at least in a longitudinal direction to form a catheter jacket comprising material from at least the filament; and
   removing the two or more elongate substrates to define a non-circular lumen through the catheter jacket along the longitudinal direction.

C2. The method according to any preceding C embodiment, further comprising inserting a plurality of spacers between the two or more elongate substrates, wherein each spacer of the plurality of spacers is spaced apart from an adjacent spacer of the plurality of spacers.

C3. The method according to embodiment C2, further comprising removing the plurality of spacers prior to removing the two or more elongate substrates.

C4. The method according to any preceding C embodiment, further comprising covering the two or more elongate substrates with a liner prior to feeding and melting the filament.

C5. The method according to any preceding C embodiment, wherein the two or more elongate substrates are positioned relative to one another to define an oblong cross-sectional shape.

C6. The method according to any preceding C embodiment, wherein the two or more elongate substrates comprises a first elongate substrate and a second elongate substrate, wherein the first elongate substrate defines a cross-sectional diameter that is different than a cross-sectional diameter of the second elongate substrate.

C7. The method according to any preceding C embodiment, further comprising:
   feeding an additional filament through another filament port into the interior cavity; and
   melting the additional filament with the filament to form the catheter jacket comprising material from at least the filament and the additional filament.

C8. The method according to embodiment C7, further comprising adjusting a ratio of the filament relative to the additional filament over a longitudinal distance to change a Shore durometer of the catheter jacket over the longitudinal distance.

Thus, various embodiments described herein are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

As used herein, the term "configured to" may be used interchangeably with the terms "adapted to" or "structured to" unless the content of this disclosure clearly dictates otherwise.

The singular forms "a," "an," and "the" encompass embodiments having plural referents unless its context clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

The invention claimed is:

1. A method for additive manufacturing of an implantable medical device, the method comprising:
feeding a substrate through a substrate channel in one or more heating cartridges, the substrate channel in fluid communication with an interior cavity of the one or more heating cartridges;
feeding at least a first filament through a filament port into the interior cavity of the one or more heating cartridges;
melting the first filament in the interior cavity of the one or more heating cartridges;
moving the one or more heating cartridges relative to the substrate at least in a longitudinal direction to form a first catheter jacket comprising material from at least the first filament;
depositing one or more internal components on the first catheter jacket;
feeding at least a second filament through a filament port into the interior cavity of the one or more heating cartridges;
melting the second filament in the interior cavity of the one or more heating cartridges;
moving the one or more heating cartridges relative to the substrate at least in the longitudinal direction to form a second catheter jacket around the first catheter jacket and the one or more internal components, wherein the second catheter jacket comprises material from at least the second filament.

2. The method of claim 1, wherein the first filament is fed into and melted within the interior cavity of a first heating cartridge of the one or more heating cartridges, and wherein the second filament is fed into and melted within the interior cavity of the first heating cartridge of the one or more heating cartridges.

3. The method of claim 2, wherein the first catheter jacket comprises material from the first and second filaments.

4. The method of claim 2, wherein the second catheter jacket comprises material from the first and second filaments.

5. The method of claim 1, wherein the first filament is fed into and melted within the interior cavity of a first heating cartridge of the one or more heating cartridges, and wherein the second filament is fed into and melted within the interior cavity of a first second heating cartridge of the one or more heating cartridges, wherein the second heating cartridge is longitudinally spaced apart from the first heating cartridge.

6. The method of claim 1, wherein forming the first catheter jacket comprises defining one or more protrusions extending from an outer surface of the first catheter jacket, wherein the one or more internal components are deposited between the one or more protrusions.

7. The method of claim 1, wherein forming the first catheter jacket comprises defining one or more channels extending inward from an outer surface of the first catheter jacket, wherein the one or more internal components are deposited within the one or more channels.

8. A method for additive manufacturing of an implantable medical device, the method comprising:
feeding a substrate through a substrate channel in one or more heating cartridges, the substrate channel in fluid communication with an interior cavity of the one or more heating cartridges;
feeding at least a first filament through a filament port into the interior cavity of the one or more heating cartridges;
melting the first filament in the interior cavity of the one or more heating cartridges;

moving the one or more heating cartridges relative to the substrate at least in a longitudinal direction to form a first catheter jacket comprising material from at least the first filament, wherein forming the first catheter jacket comprises defining one or more protrusions extending from an outer surface of the first catheter jacket;

depositing one or more internal components on the first catheter jacket, wherein the one or more internal components are deposited between the one or more protrusions;

feeding at least a second filament through a filament port into the interior cavity of the one or more heating cartridges;

melting the second filament in the interior cavity of the one or more heating cartridges;

moving the one or more heating cartridges relative to the substrate at least in the longitudinal direction to form a second catheter jacket around the first catheter jacket and the one or more internal components, wherein the second catheter jacket comprises material from at least the second filament.

9. The method of claim 8, wherein the first filament is fed into and melted within the interior cavity of a first heating cartridge of the one or more heating cartridges, and wherein the second filament is fed into and melted within the interior cavity of the first heating cartridge of the one or more heating cartridges.

10. The method of claim 9, wherein the first catheter jacket comprises material from the first and second filaments.

11. The method of claim 9, wherein the second catheter jacket comprises material from the first and second filaments.

12. The method of claim 8, wherein the first filament is fed into and melted within the interior cavity of a first heating cartridge of the one or more heating cartridges, and wherein the second filament is fed into and melted within the interior cavity of a second heating cartridge of the one or more heating cartridges, wherein the second heating cartridge is longitudinally spaced apart from the first heating cartridge.

13. A method for additive manufacturing of an implantable medical device, the method comprising:

feeding a substrate through a substrate channel in one or more heating cartridges, the substrate channel in fluid communication with an interior cavity of the one or more heating cartridges;

feeding at least a first filament through a filament port into the interior cavity of the one or more heating cartridges;

melting the first filament in the interior cavity of the one or more heating cartridges;

moving the one or more heating cartridges relative to the substrate at least in a longitudinal direction to form a first catheter jacket comprising material from at least the first filament, wherein forming the first catheter jacket comprises defining one or more channels extending inward from an outer surface of the first catheter jacket;

depositing one or more internal components on the first catheter jacket, wherein the one or more internal components are deposited within the one or more channels;

feeding at least a second filament through a filament port into the interior cavity of the one or more heating cartridges;

melting the second filament in the interior cavity of the one or more heating cartridges;

moving the one or more heating cartridges relative to the substrate at least in the longitudinal direction to form a second catheter jacket around the first catheter jacket and the one or more internal components, wherein the second catheter jacket comprises material from at least the second filament.

14. The method of claim 13, wherein the first filament is fed into and melted within the interior cavity of a first heating cartridge of the one or more heating cartridges, and wherein the second filament is fed into and melted within the interior cavity of the first heating cartridge of the one or more heating cartridges.

15. The method of claim 14, wherein the first catheter jacket comprises material from the first and second filaments.

16. The method of claim 14, wherein the second catheter jacket comprises material from the first and second filaments.

17. The method of claim 13, wherein the first filament is fed into and melted within the interior cavity of a first heating cartridge of the one or more heating cartridges, and wherein the second filament is fed into and melted within the interior cavity of a second heating cartridge of the one or more heating cartridges, wherein the second heating cartridge is longitudinally spaced apart from the first heating cartridge.

* * * * *